United States Patent
Thomas

(10) Patent No.: US 8,466,181 B2
(45) Date of Patent: Jun. 18, 2013

(54) 1,2,3-TRIAZOLE-IMIDAZOLE COMPOUNDS

(75) Inventor: Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 90 days.

(21) Appl. No.: 13/309,589

(22) Filed: Dec. 2, 2011

(65) Prior Publication Data

US 2012/0149675 A1    Jun. 14, 2012

(30) Foreign Application Priority Data

Dec. 10, 2010   (EP) .................................... 10194496

(51) Int. Cl.
*C07D 249/00*    (2006.01)

(52) U.S. Cl.
USPC .......................................... 514/359; 548/255

(58) Field of Classification Search
USPC .......................................... 514/359; 548/255
See application file for complete search history.

(56) References Cited

U.S. PATENT DOCUMENTS

2009/0005370 A1\* 1/2009 Buettelmann et al. ..... 514/227.8
2009/0143407 A1   6/2009 Buettelmann et al.

OTHER PUBLICATIONS

Cui et al., "Cell" 135:549-560 ( 2008).
Rueda et al., "Neuroscience Letters" 433:22-27 ( 2008).
"International Search Report PCT/EP2011/072041 mailed Jan. 19, 2012".
Fernandez et al., "Nature Neuroscience" 10:411-413 ( 2007).
McCauley et al., "Genetics" 131B:51-59 ( 2004).
Otani et al., "Neuroscience Letters" 381:108-113 ( 2005).
Papadimitriou et al., "Neuropsychobiology" 43(3):1410144 ( 2001).
Delong et al., "Autism" 11(2):135-147 ( 2007).
McKernan et al., "Recombinant Cell Surface Receptors: Focal Point for Therapeutic Intervention" (M. J. Browne (Ed.), R. G. Landes Co., Austin, Texas), 8:155-173 (1997).
Oyama, et al., "Psychobiology" 21:101-105 ( 1998).
Solis-Anez et al., "Investigacion Clinica" 48:529-541 ( 2007).

\* cited by examiner

*Primary Examiner* — Susannah Chung

(57) ABSTRACT

The present invention is concerned with novel 1,2,3-triazole-imidazole compounds of formula (I)

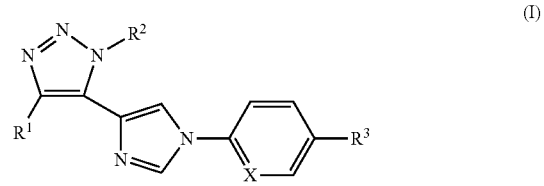

wherein X, $R^1$, $R^2$, and $R^3$ are as described herein, as well as pharmaceutically acceptable salts and esters thereof. The active compounds of present invention have affinity and selectivity for the GABA A α5 receptor. Further the present invention provides a method for the manufacture of the compounds of formula (I), pharmaceutical compositions comprising them and their use as therapeutic agents.

22 Claims, No Drawings

1,2,3-TRIAZOLE-IMIDAZOLE COMPOUNDS

PRIORITY TO RELATED APPLICATION(S)

This application claims the benefit of European Patent Application No. 10194496.5, filed Dec. 10, 2010, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits. Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I benzodiazepine receptor (BzR) subtypes, whereas α2β2γ2, α3β2γ2 and α5β2γ2 ion channels are termed type-II BzR (R. M. McKernan, P. J. Whiting, in *Recombinant Cell Surface Receptors: Focal Point for Therapeutic Intervention*, M. J. Browne (Ed.) (1997) Chapter 8:155-173, R.G. Landes Co., Austin, Tex.).

It has been shown by McNamara and Skelton (*Psychobiology* (1993) 21:101-108) that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

Literature has been published to establish the link between GABA A α5 subunits and the treatment of various diseases of the Central Nervous System (*Neuroscience Letts.* (2005) 381: 108-13, *Neuropsychobiology* (2001) 43(3):141-44, *Amer. J. Med. Genetics* (2004) 131B:51-9, *Autism* (2007) 11(2):135-47, *Investigacion Clinica* (2007) 48:529-41, *Nature Neuroscience* (2007) 10:411-13, *Neuroscience Letts.* (2008) 433: 22-7, *Cell* (2008) 135:549-60).

SUMMARY OF THE INVENTION

The present invention provides 1,2,3-triazole-imidazole compounds having affinity and selectivity for the GABA A α5 receptor, their manufacture, pharmaceutical compositions comprising them and their use as pharmaceuticals.

The present invention provides compounds of formula (I)

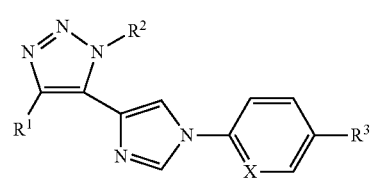

(I)

wherein X, $R^1$, $R^2$ and $R^3$ are as described below and in the claims, and pharmaceutically acceptable salts and esters thereof.

The present invention provides compounds of formula (I) and their pharmaceutically acceptable salts and esters, the preparation of the above mentioned compounds, pharmaceutical compositions containing them and their manufacture as well as the use of the above mentioned compounds in the treatment or prevention of diseases related to the GABA A α5. The compounds of present invention are preferably inverse agonists of GABA A α5.

The compounds of present invention and their pharmaceutically acceptable salts and esters have high affinity and selectivity for the GABA A α5 receptor and can be used, alone or in combination with other drugs, as cognitive enhancers or for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety.

The nomenclature used in this application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkyl-aryl", "haloalkyl-heteroaryl", "arylalkyl-heterocycloalkyl", or "alkoxy-alkyl". The last member of the combination is a radical which is substituted by the other members of the combination in inverse order.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance may, but need not, occur and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds of formula (I) and stereoisomers, tautomers, solvates, and salts (e.g., pharmaceutically acceptable salts) thereof.

It will be appreciated, that the compounds of present invention can be derivatized at functional groups to provide derivatives which are capable of conversion back to the parent compound in vivo. Physiologically acceptable and metabolically labile derivatives, which are capable of producing the parent compounds of present invention in vivo are also within the scope of this invention.

The term "pharmaceutically acceptable esters" denotes derivatives of the compounds of present invention, in which a carboxy group has been converted to an ester, wherein carboxy group means —C(O)O—. Methyl-, ethyl-, methoxymethyl-, methylthiomethyl-, and pivaloyloxymethylesters are examples of such suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, and which are non toxic to living organisms.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "solvate" denotes crystal forms having either stoichiometric or nonstoichiometric amounts of a solvent incorporated in the crystal lattice. If the incorporated solvent is water, the solvate formed is a hydrate. When the incorporated solvent is alcohol, the solvate formed is an alcoholate.

The term "halo", "halogen", and "halide" are used interchangeably herein and denote fluoro, chloro, bromo, or iodo. Particular examples for halo are fluoro and chloro, most particularly fluoro.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, or tert-butyl. Particular examples for alkyl are methyl, isopropyl, iso-butyl, and tert-butyl, most particularly methyl and isopropyl.

The term "alkoxy" denotes a group of the formula —O—R', wherein R' is an alkyl group. Examples of alkoxy moieties include methoxy, ethoxy, isopropoxy, and tert-butoxy. Particular example for alkoxy is methoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples for haloalkyl is trifluoro-methyl.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl. Particular examples for hydroxyalkyl are hydroxyisobutyl and hydroxytert-butyl, more particularly 2-hydroxy-2-methylpropyl and 1-hydroxy-2-methylpropan-2-yl, most particularly 1-hydroxy-2-methylpropan-2-yl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. Particular example for cycloalkyl is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl. Particular example for cycloalkylalkyl is cyclopropylmethyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydropyridinyl, or dihydropyranyl. Heterocycloalkyl can optionally substituted as described herein, particularly substituted by one or more alkyl or oxo. Particular examples for heterocycloalkyl are morpholinyl, oxetanyl, tetrahydropyranyl, thiomorpholinyl and 2-oxa-6-aza-spiro[3.3]hept-6-yl, more particularly morpholinyl, 3-methyl-oxetan-3-yl, tetrahydro-pyran-4-yl, 1,1-dioxo-1,6-thiomorpholin-4-yl, and 2-oxa-6-aza-spiro[3.3]hept-6-yl. Most particular examples for heterocycloalkyl are 3-methyl-oxetan-3-yl, tetrahydro-pyran-4-yl and 2-oxa-6-aza-spiro[3.3]hept-6-yl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl. Particular example for aryl is phenyl.

The term "aryloxy" denotes a group of the formula —O—R', wherein R' is aryl. An example of aryloxy is phenoxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "oxo" denotes a divalent oxygen atom =O.

The term "active pharmaceutical ingredient" (or "API") denotes the compound in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutical composition" (or "composition") denotes a mixture or solution comprising a therapeutically effective amount of an active pharmaceutical ingredient together with pharmaceutically acceptable excipients to be administered to a mammal, e.g., a human in need thereof.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

The term "treating" or "treatment" of a disease state includes (1) preventing the disease state, i.e. causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

The term "subject" denotes a vertebrate. In certain embodiments, the vertebrate is a mammal. Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

In particular, the present invention provides compounds of formula (I)

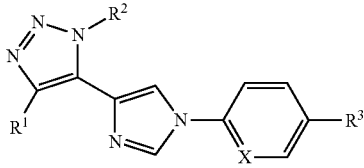

(I)

wherein
X is N or CH;
R¹ and R² are each independently alkyl, aryl optionally substituted by 1 or 2 halo, or heteroaryl optionally substituted by 1 or 2 halo, wherein one of R¹ and R² is alkyl;
R³ is halo, alkyl, haloalkyl, hydroxyalkyl, cyano, nitro, —C(O)R⁴, or —C(O)NR⁵R⁶;
R⁴ is hydrogen, alkyl, aryl, hydroxy, alkoxy or aryloxy;
R⁵ is hydrogen, alkyl, haloalkyl, hydroxyalkyl, —(CH$_2$)$_n$-cycloalkyl, —(CH$_2$)$_n$-heterocycloalkyl, —(CH$_2$)$_n$-aryl, —(CH$_2$)$_n$-heteroaryl, —(CH$_2$)$_m$—NR⁷R⁸, —(CH$_2$)$_m$—OR⁹, wherein cycloalkyl, heterocycloalkyl, aryl and heteroaryl are each optionally substituted by one or more halo, alkyl, haloalkyl, hydroxyalkyl, alkoxy, hydroxy, or oxo;
n is an integer from 0 to 6;
m is an integer from 2 to 6;
R⁶, R⁷, R⁸, and R⁹ are each independently hydrogen, alkyl, or aryl;
or R⁵ and R⁶ together with the nitrogen to which they are bound form a heterocycloalkyl or heteroaryl, wherein heterocycloalkyl and heteroaryl are each optionally substituted by one or more halo, alkyl, haloalkyl, hydroxyalkyl, alkoxy, hydroxy, or oxo;
and pharmaceutically acceptable salts and esters thereof.

Particular embodiments of present invention are compounds of formula (I) and pharmaceutically acceptable salts and esters thereof.

Further, it is to be understood that every embodiment relating to a specific residue X, R¹, R², R³, R⁴, R⁵, R⁶, R⁷, R⁸, R⁹, n, or m as disclosed herein can be combined with any other embodiment relating to another residue X, R¹, R², R³, R⁴, R⁵, R⁶, R⁷, R⁸, R⁹, n, or m as disclosed herein.

A particular embodiment of the present invention provides compounds of formula (I), wherein
X is N or CH;
R¹ and R² are each independently alkyl, or aryl optionally substituted by 1 halo, wherein one of R¹ and R² is alkyl;
R³ is haloalkyl, nitro, —C(O)R⁴, or —C(O)NR⁵R⁶;
R⁴ is alkyl, hydroxy, or alkoxy;
R⁵ is hydrogen, alkyl, hydroxyalkyl, —(CH$_2$)$_n$-cycloalkyl, or —(CH$_2$)$_n$-heterocycloalkyl, wherein heterocycloalkyl is optionally substituted by one alkyl;
n is an integer from 0 to 1;
R⁶ is hydrogen;
or R⁵ and R⁶ together with the nitrogen to which they are bound form a heterocycloalkyl optionally substituted by one or more oxo;
and pharmaceutically acceptable salts and esters thereof.

A particular embodiment of the present invention provides compounds of formula (Ia)

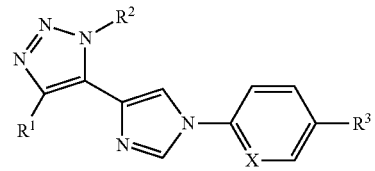

(Ia)

wherein R¹, R² and R³ are as described herein.

A particular embodiment of the present invention provides compounds of formula (Ib)

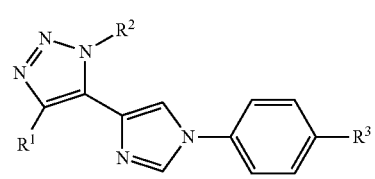

(Ib)

wherein R¹, R² and R³ are as described herein.

In a particular embodiment of the invention, X is N.
In a particular embodiment of the invention, X is CH.
In a particular embodiment of the invention, one of R¹ and R² is alkyl, and the other one is aryl optionally substituted by one halo.
In a particular embodiment of the invention, one of R¹ and R² is methyl, and the other one is phenyl optionally substituted by one fluoro or chloro.
In a particular embodiment of the invention, one of R¹ and R² is methyl, and the other one is phenyl substituted by one fluoro.
In a particular embodiment of the invention, R¹ is alkyl; and R² is aryl substituted by one halo.
In a particular embodiment of the invention, R¹ is methyl, and R² is phenyl substituted by one fluoro.
In a particular embodiment of the invention, R² is alkyl; and R¹ is aryl substituted by one halo.
In a particular embodiment of the invention, R² is methyl, and R¹ is phenyl substituted by one fluoro.
In a particular embodiment of the invention, R³ is haloalkyl, nitro, —C(O)R⁴, or —C(O)NR⁵R⁶.
In a particular embodiment of the invention, R³ is trifluoromethyl, nitro, —C(O)R⁴, or —C(O)NR⁵R⁶.
In a particular embodiment of the invention, R³ is trifluoromethyl.
In a particular embodiment of the invention, R³ is —C(O)NR⁵R⁶.
In a particular embodiment of the invention, R⁴ is alkyl, hydroxy, or alkoxy.
In a particular embodiment of the invention, R⁴ is methyl, hydroxy, or methoxy.
In a particular embodiment of the invention, R⁵ is hydrogen, alkyl, hydroxyalkyl, —(CH$_2$)$_n$-cycloalkyl, or —(CH$_2$)$_n$-heterocycloalkyl, wherein heterocycloalkyl is optionally substituted by one alkyl.
In a particular embodiment of the invention, R⁵ is hydrogen, isopropyl, iso-butyl substituted by hydroxy, tert-butyl substituted by hydroxy, cyclopropyl, cyclopropylmethyl, morpholinyl, tetrahydropyranyl, or oxetanyl substituted by methyl.
In a particular embodiment of the invention, R⁵ is isopropyl, tert-butyl substituted by hydroxy, cyclopropyl, tetrahydropyranyl, or oxetanyl substituted by methyl.

In a particular embodiment of the invention, $R^6$ is hydrogen.

In a particular embodiment of the invention, $R^5$ and $R^6$ together with the nitrogen to which they are bound form a heterocycloalkyl optionally substituted by one or more oxo.

In a particular embodiment of the invention, $R^5$ and $R^6$ together with the nitrogen to which they are bound form 1,1-dioxo-1,6-thiomorpholin-4-yl or 2-oxa-6-aza-spiro[3.3]hept-6-yl.

In a particular embodiment of the invention, $R^5$ and $R^6$ together with the nitrogen to which they are bound form 2-oxa-6-aza-spiro[3.3]hept-6-yl.

A particular embodiment of the present invention provides compounds of formula (I) as described in the examples as individual compounds as well as pharmaceutically acceptable salts and esters thereof. Furthermore, the substituents as found in the specific examples described below, individually constitute separate particular embodiments of the present invention.

Particular compounds of formula (I) of present invention are those selected from the group consisting of:

1-(4-{4-[5-(4-Fluoro-phenyl)-3-methyl-3H-[1,2,3]triazol-4-yl]-imidazol-1-yl}-phenyl)-ethanone;
4-{4-[5-(4-Fluoro-phenyl)-3-methyl-3H-[1,2,3]triazol-4-yl]-imidazol-1-yl}-benzoic acid methyl ester;
4-{4-[5-(4-Fluoro-phenyl)-3-methyl-3H-[1,2,3]triazol-4-yl]-imidazol-1-yl}-N-isopropyl-benzamide;
4-{4-[5-(4-Fluoro-phenyl)-3-methyl-3H-[1,2,3]triazol-4-yl]-imidazol-1-yl}-N-(tetrahydro-pyran-4-yl)-benzamide;
4-{4-[5-(4-Fluoro-phenyl)-3-methyl-3H-[1,2,3]triazol-4-yl]-imidazol-1-yl}-N-(3-methyl-oxetan-3-yl)-benzamide;
(4-{4-[5-(4-Fluoro-phenyl)-3-methyl-3H-[1,2,3]triazol-4-yl]-imidazol-1-yl}-phenyl)-(2-oxa-6-aza-spiro[3.3]hept-6-yl)-methanone;
4-{4-[5-(4-Fluoro-phenyl)-3-methyl-3H-[1,2,3]triazol-4-yl]-imidazol-1-yl}-benzamide;
4-(2-Fluorophenyl)-1-methyl-5-(1-(4-(trifluoromethyl)phenyl)-1H-imidazol-4-yl)-1H-1,2,3-triazole;
4-(2-Fluorophenyl)-1-methyl-5-(1-(4-nitrophenyl)-1H-imidazol-4-yl)-1H-1,2,3-triazole;
1-(4-(4-(4-(2-Fluorophenyl)-1-methyl-1H-1,2,3-triazol-5-yl)-1H-imidazol-1-yl)phenyl)ethanone;
6-{4-[5-(4-Fluoro-phenyl)-3-methyl-3H-[1,2,3]triazol-4-yl]-imidazol-1-yl}-N-isopropyl-nicotinamide;
6-{4-[5-(4-Fluoro-phenyl)-3-methyl-3H-[1,2,3]triazol-4-yl]-imidazol-1-yl}-N-(tetrahydro-pyran-4-yl)-nicotinamide;
6-{4-[5-(4-Fluoro-phenyl)-3-methyl-3H-[1,2,3]triazol-4-yl]-imidazol-1-yl}-N-(3-methyl-oxetan-3-yl)-nicotinamide;
(6-{4-[5-(4-Fluoro-phenyl)-3-methyl-3H-[1,2,3]triazol-4-yl]-imidazol-1-yl}-pyridin-3-yl)-(2-oxa-6-aza-spiro[3.3]hept-6-yl)-methanone;
2-{4-[5-(4-Fluoro-phenyl)-3-methyl-3H-[1,2,3]triazol-4-yl]-imidazol-1-yl}-5-trifluoromethyl-pyridine;
6-(4-(4-(4-Fluorophenyl)-1-methyl-1H-1,2,3-triazol-5-yl)-1H-imidazol-1-yl)nicotinamide;
Methyl 6-(4-(4-(2-chlorophenyl)-1-methyl-1H-1,2,3-triazol-5-yl)-1H-imidazol-1-yl)nicotinate;
6-(4-(4-(2-Chlorophenyl)-1-methyl-1H-1,2,3-triazol-5-yl)-1H-imidazol-1-yl)-N-isopropylnicotinamide;
6-(4-(4-(2-Chlorophenyl)-1-methyl-1H-1,2,3-triazol-5-yl)-1H-imidazol-1-yl)nicotinamide;
Methyl 6-(4-(4-(2-fluorophenyl)-1-methyl-1H-1,2,3-triazol-5-yl)-1H-imidazol-1-yl)nicotinate;
6-(4-(4-(2-Fluorophenyl)-1-methyl-1H-1,2,3-triazol-5-yl)-1H-imidazol-1-yl)nicotinic acid;
6-(4-(4-(2-Fluorophenyl)-1-methyl-1H-1,2,3-triazol-5-yl)-1H-imidazol-1-yl)-N-(tetrahydro-2H-pyran-4-yl)nicotinamide;
6-(4-(4-(2-Fluorophenyl)-1-methyl-1H-1,2,3-triazol-5-yl)-1H-imidazol-1-yl)-N-isopropylnicotinamide;
6-(4-(4-(2-Fluorophenyl)-1-methyl-1H-1,2,3-triazol-5-yl)-1H-imidazol-1-yl)-N-(2-hydroxy-2-methylpropyl)nicotinamide;
6-(4-(4-(2-Fluorophenyl)-1-methyl-1H-1,2,3-triazol-5-yl)-1H-imidazol-1-yl)nicotinamide;
(6-(4-(4-(2-Fluorophenyl)-1-methyl-1-1,2,3-triazol-5-yl)-1H-imidazol-1-yl)pyridin-3-yl)(2-oxa-6-azaspiro[3.3]heptan-6-yl)methanone;
6-(4-(4-(2-Fluorophenyl)-1-methyl-1H-1,2,3-triazol-5-yl)-1H-imidazol-1-yl)-N-(3-methyloxetan-3-yl)nicotinamide;
6-(4-(4-(2-Fluorophenyl)-1-methyl-1H-1,2,3-triazol-5-yl)-1H-imidazol-1-yl)-N-morpholinonicotinamide;
N-Cyclopropyl-6-(4-(4-(2-fluorophenyl)-1-methyl-1H-1,2,3-triazol-5-yl)-1H-imidazol-1-yl)nicotinamide;
2-(4-(4-(2-Fluorophenyl)-1-methyl-1H-1,2,3-triazol-5-yl)-1H-imidazol-1-yl)-5-(trifluoromethyl)pyridine;
1-(4-Fluoro-phenyl)-4-methyl-5-[1-(4-trifluoromethyl-phenyl)-1H-imidazol-4-yl]-1H-[1,2,3]triazole;
1-(4-{4-[3-(4-Fluoro-phenyl)-5-methyl-3H-[1,2,3]triazol-4-yl]-imidazol-1-yl}-phenyl)-ethanone;
Methyl 4-(4-(1-(2-fluorophenyl)-4-methyl-1H-1,2,3-triazol-5-yl)-1H-imidazol-1-yl)benzoate;
2-{4-[3-(4-Fluoro-phenyl)-5-methyl-3H-[1,2,3]triazol-4-yl]-imidazol-1-yl}-5-trifluoromethyl-pyridine;
Methyl 6-(4-(1-(4-fluorophenyl)-4-methyl-1H-1,2,3-triazol-5-yl)-1H-imidazol-1-yl)nicotinate;
6-(4-(1-(4-Fluorophenyl)-4-methyl-1H-1,2,3-triazol-5-yl)-1H-imidazol-1-yl)-N-isopropylnicotinamide;
6-{4-[3-(4-Fluoro-phenyl)-5-methyl-3H-[1,2,3]triazol-4-yl]-imidazol-1-yl}-N-(tetrahydro-pyran-4-yl)-nicotinamide;
6-(4-(1-(4-Fluorophenyl)-4-methyl-1H-1,2,3-triazol-5-yl)-1H-imidazol-1-yl)-N-(3-methyloxetan-3-yl)nicotinamide;
(6-(4-(1-(4-Fluorophenyl)-4-methyl-1H-1,2,3-triazol-5-yl)-1H-imidazol-1-yl)pyridin-3-yl)(2-oxa-6-azaspiro[3.3]heptan-6-yl)methanone;
6-(4-(1-(4-Fluorophenyl)-4-methyl-1H-1,2,3-triazol-5-yl)-1H-imidazol-1-yl)nicotinamide;
6-(4-(1-(4-Fluorophenyl)-4-methyl-1H-1,2,3-triazol-5-yl)-1H-imidazol-1-yl)-N-(1-hydroxy-2-methylpropan-2-yl)nicotinamide;
N-Cyclopropyl-6-(4-(1-(4-fluorophenyl)-4-methyl-1H-1,2,3-triazol-5-yl)-1H-imidazol-1-yl)nicotinamide;
6-(4-(1-(2-Fluorophenyl)-4-methyl-1H-1,2,3-triazol-5-yl)-1H-imidazol-1-yl)-N-isopropylnicotinamide;
(1,1-Dioxo-1,6-thiomorpholin-4-yl)-(6-{4-[3-(4-fluoro-phenyl)-5-methyl-3H-[1,2,3]triazol-4-yl]-imidazol-1-yl}-pyridin-3-yl)-methanone;
6-(4-(1-(4-Fluorophenyl)-4-methyl-1H-1,2,3-triazol-5-yl)-1H-imidazol-1-yl)-N-morpholinonicotinamide;
6-(4-(1-(2-Fluorophenyl)-4-methyl-1H-1,2,3-triazol-5-yl)-1H-imidazol-1-yl)-N-(tetrahydro-2H-pyran-4-yl)nicotinamide;
6-(4-(1-(2-Fluorophenyl)-4-methyl-1H-1,2,3-triazol-5-yl)-1H-imidazol-1-yl)-N-(1-hydroxy-2-methylpropan-2-yl)nicotinamide;
6-(4-(1-(2-Fluorophenyl)-4-methyl-1H-1,2,3-triazol-5-yl)-1H-imidazol-1-yl)nicotinamide;

(6-(4-(1-(2-Fluorophenyl)-4-methyl-1-1,2,3-triazol-5-yl)-1H-imidazol-1-yl)pyridin-3-yl)(2-oxa-6-azaspiro[3.3]heptan-6-yl)methanone;

6-(4-(1-(2-Fluorophenyl)-4-methyl-1H-1,2,3-triazol-5-yl)-1H-imidazol-1-yl)-N-(3-methyloxetan-3-yl)nicotinamide;

6-(4-(1-(2-Fluorophenyl)-4-methyl-1H-1,2,3-triazol-5-yl)-1H-imidazol-1-yl)-N-morpholinonicotinamide;

N-Cyclopropyl-6-(4-(1-(2-fluorophenyl)-4-methyl-1H-1,2,3-triazol-5-yl)-1H-imidazol-1-yl)nicotinamide;

N-(Cyclopropylmethyl)-6-(4-(1-(2-fluorophenyl)-4-methyl-1H-1,2,3-triazol-5-yl)-1H-imidazol-1-yl)nicotinamide;

and pharmaceutically acceptable salts and esters thereof.

Particular compounds of formula (I) of present invention are those selected from the group consisting of:

4-{4-[5-(4-Fluoro-phenyl)-3-methyl-3H-[1,2,3]triazol-4-yl]-imidazol-1-yl}-N-isopropyl-benzamide;

6-{4-[5-(4-Fluoro-phenyl)-3-methyl-3H-[1,2,3]triazol-4-yl]-imidazol-1-yl}-N-isopropyl-nicotinamide;

6-{4-[5-(4-Fluoro-phenyl)-3-methyl-3H-[1,2,3]triazol-4-yl]-imidazol-1-yl}-N-(3-methyl-oxetan-3-yl)-nicotinamide;

(6-{4-[5-(4-Fluoro-phenyl)-3-methyl-3H-[1,2,3]triazol-4-yl]-imidazol-1-yl}-pyridin-3-yl)-(2-oxa-6-aza-spiro[3.3]hept-6-yl)-methanone;

2-{4-[3-(4-Fluoro-phenyl)-5-methyl-3H-[1,2,3]triazol-4-yl]-imidazol-1-yl}-5-trifluoromethyl-pyridine;

6-(4-(1-(4-Fluorophenyl)-4-methyl-1H-1,2,3-triazol-5-yl)-1H-imidazol-1-yl)-N-isopropylnicotinamide;

6-{4-[3-(4-Fluoro-phenyl)-5-methyl-3H-[1,2,3]triazol-4-yl]-imidazol-1-yl}-N-(tetrahydro-pyran-4-yl)-nicotinamide;

6-(4-(1-(4-Fluorophenyl)-4-methyl-1H-1,2,3-triazol-5-yl)-1H-imidazol-1-yl)-N-(3-methyloxetan-3-yl)nicotinamide;

(6-(4-(1-(4-Fluorophenyl)-4-methyl-1H-1,2,3-triazol-5-yl)-1H-imidazol-1-yl)pyridin-3-yl)(2-oxa-6-azaspiro[3.3]heptan-6-yl)methanone;

6-(4-(1-(4-Fluorophenyl)-4-methyl-1H-1,2,3-triazol-5-yl)-1H-imidazol-1-yl)-N-(1-hydroxy-2-methylpropan-2-yl)nicotinamide; and N-Cyclopropyl-6-(4-(1-(4-fluorophenyl)-4-methyl-1H-1,2,3-triazol-5-yl)-1H-imidazol-1-yl)nicotinamide;

and pharmaceutically acceptable salts and esters thereof.

The invention further provides a process for the preparation of compounds of formula (I) as defined herein, comprising the reaction of a compound of formula (II)

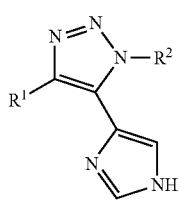
(II)

with a compound of formula (III)

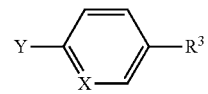
(III)

wherein X, $R^1$, $R^2$ and $R^3$ are as defined herein and Y is fluoro or chloro.

The invention further provides compounds of formula (I) as defined above obtainable by a process as described above.

Compounds of formula (I) can be prepared following standard methods as described below, wherein X, $R^1$, $R^2$ and $R^3$ are as described above and in the claims, unless mentioned otherwise.

Scheme 1

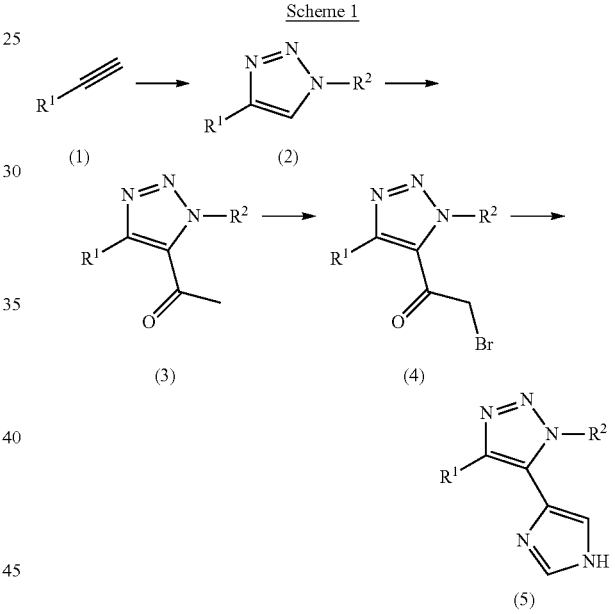

According to Scheme 1, a compound of formula (1) can be treated with Cu(I)I, sodium azide and a compound of formula $IR^2$ in the presence of ascorbic acid to give a compound of formula (2). Compounds of formula (2) can then be treated with a strong base, such as BuLi, in a suitable solvent, such as DME, at reduced temperatures, such as −75° C. to −35° C., and then reacted with CuCN in the presence of LiCl in a suitable solvent, such as THF, at −75° C. and then reacted with acetylchloride to give a compound of formula (3). Compounds of formula 3 can then be treated with bromine in a suitable solvent such as chloroform and acetic acid to give a compound of formula (4). Further reaction of compounds of formula (4) with formamide in the presence of water under heating, e.g. conventional heating or microwave heating at 140° C., gives a product of formula (5).

Scheme 2

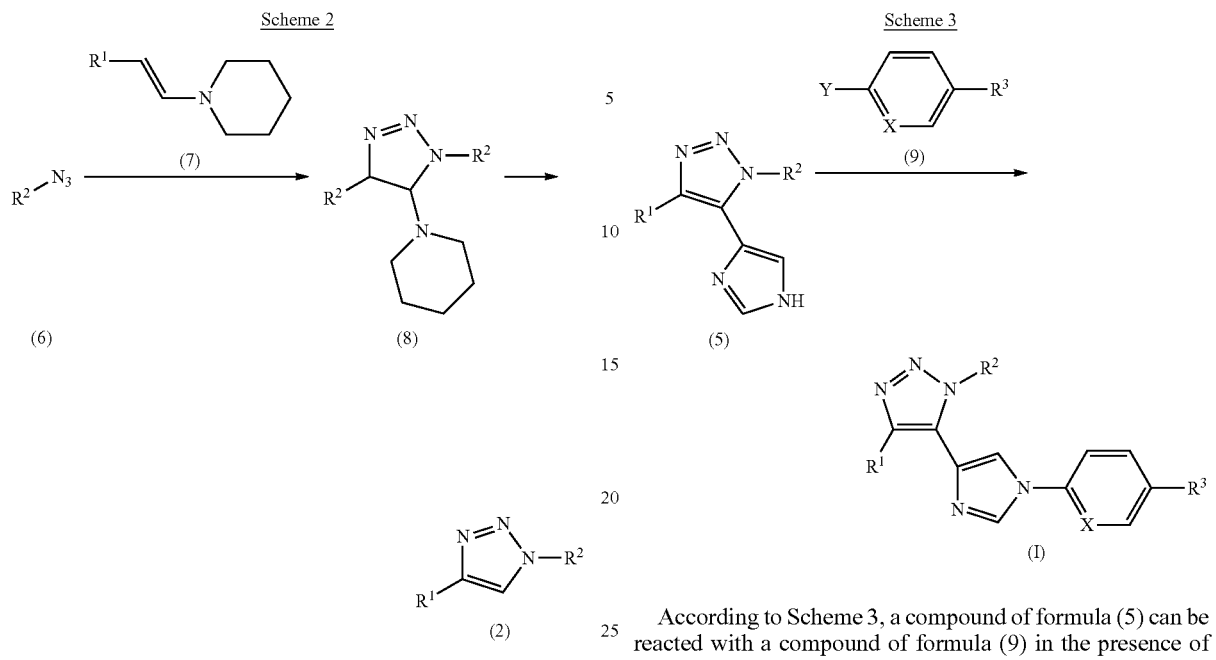

Alternatively, according to Scheme 2, compounds of formula (6) can be treated with compounds of formula (7) to give compounds of formula (8), which upon treatment with a base, such as potassium hydroxide, in a suitable solvent, such as methanol, give compounds of formula (2).

According to Scheme 3, a compound of formula (5) can be reacted with a compound of formula (9) in the presence of potassium carbonate, in a suitable solvent, such as DMF, at elevated temperatures, such as +80° C. to +160° C., to give a compound of formula (I), wherein Y is fluoro or chloro.

In accordance with Scheme 4, compounds of formula (I) wherein $R^3$ is —C(O)NR$^5$R$^6$ can be prepared following standard methods from compounds of formula (I) wherein $R^3$ is —C(O)R$^4$.

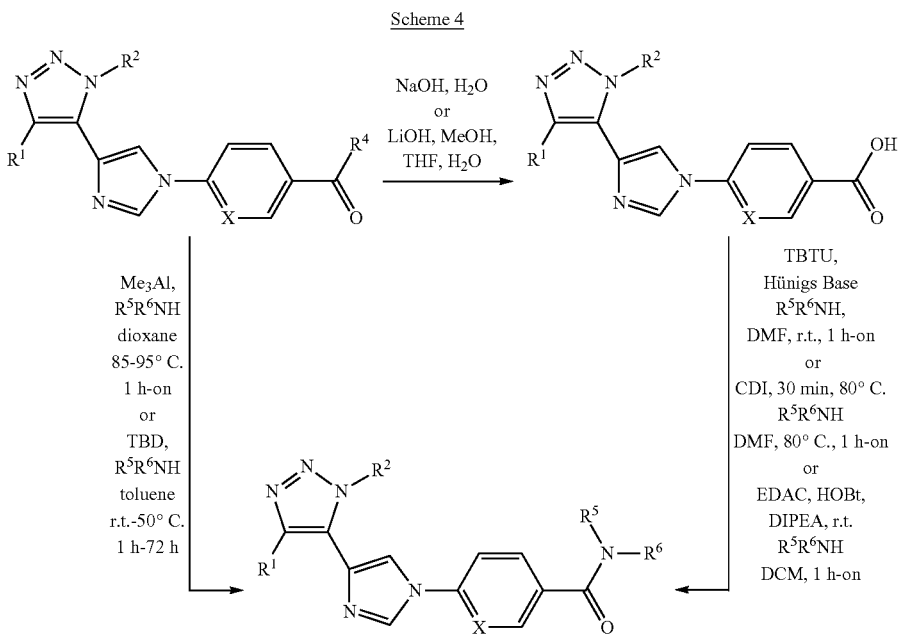

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

The present invention also provides compounds of formula (I) as defined above, when prepared by a process as described above.

| | |
|---|---|
| BuLi = | n-butyllithium |
| CDI = | 1,1'-carbonyldiimidazole |
| DCM = | dichloromethane |
| DIPEA = | N,N-diisopropylethylamine (Hünigs Base) |
| DMF = | dimethylformamid |
| DME = | dimethoxyethane |
| EDAC = | 1-ethyl-3-(3-dimethylaminopropyl) carbodiimide hydrochloride |
| HOBt = | hydroxybenzotriazole |
| hv = | high vacuum |
| on = | overnight |
| r.t. = | room temperature |
| TBD = | 1,5,7-triazabicyclo[4.4.0]dec-5-ene |
| TBTU = | O-(benzotriazol-1-y1)-N,N,N',N'-tetramethyluronium tetrafluoroborate |
| THF = | tetrahydrofuran |

Another embodiment provides pharmaceutical compositions or medicaments comprising the compounds of the invention and a therapeutically inert carrier, diluent or excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention can be administered in any convenient administrative form, e.g., tablets, powders, capsules, solutions, dispersions, suspensions, syrups, sprays, suppositories, gels, emulsions, patches, etc. Such compositions can comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.1 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution can be filtered, e.g., using a 0.2 μm filter, to remove impurities and contaminants.

As described above, the novel compounds of the present invention and their pharmaceutically acceptable salts and esters possess valuable pharmacological properties and are ligands for GABA A α5 receptors. The compounds of the present invention can therefore be used, either alone or in combination with other drugs, for the treatment or prevention of diseases which are modulated by ligands for GABA A receptors containing the α5 subunit. These diseases include, but are not limited to acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, attentional disorders and need for cognition enhancement.

The invention therefore also provides pharmaceutical compositions comprising a compound as defined above and a pharmaceutically acceptable excipient.

The invention likewise embraces compounds as described above for use as therapeutically active substances.

The invention likewise embraces compounds as described above for use as therapeutically active substances for the treatment or prevention of diseases which are related to the GABA A α5 receptor.

The invention likewise embraces compounds as described above for use as therapeutically active substances for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders or for use as cognitive enhancers.

The invention likewise embraces compounds as described above for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

In another embodiment, the invention provides a method for the treatment or prevention of diseases which are related to the GABA A α5 receptor.

In another embodiment, the invention provides a method for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders or for cognition enhancement, which method comprises administering a compound as defined above to a human being or animal.

The invention also embraces the use of compounds as defined above for the treatment or prevention of diseases which are related to the GABA A α5 receptor.

The invention also embraces the use of compounds as defined above for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders or for cognition enhancement.

The invention also provides the use of compounds as described above for the preparation of medicaments for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders or for the preparation of cognitive enhancers. Such medicaments comprise a compound as described above.

More particularly, the present invention provides the use of compounds as described above for the treatment, prevention and/or delay of progression of CNS conditions caused by neurodevelopmental defects which result in excessive GABAergic inhibition in the cortex and hippocampus, wherein the CNS condition is selected from cognitive deficits in Down Syndrome, in autism, in neurofibromatosis type I, or after stroke.

The treatment or prevention of cognitive disorders, Alzheimer's disease, schizophrenia, positive, negative and/or cognitive symptoms associated with schizophrenia, Down syndrome, and neurofibromatosis type I, are particular embodiments of present invention.

A particular embodiment of the invention embraces the treatment or prevention of Alzheimer's disease.

A particular embodiment of the invention embraces the treatment or prevention of Down syndrome.

A particular embodiment of the invention embraces the treatment or prevention of neurofibromatosis type I.

The invention will be more fully understood by reference to the following examples. They should not, however, be construed as limiting the scope of the invention.

Example 1

1-(4-{4-[5-(4-Fluoro-phenyl)-3-methyl-3H-[1,2,3]
triazol-4-yl]-imidazol-1-yl}-phenyl)-ethanone

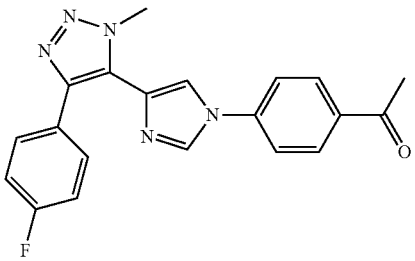 [SMILES: CC(=O)c1ccc(-n2cnc(-c3c(-c4ccc(F)cc4)nnn3C)c2)cc1]

4-(4-Fluoro-phenyl)-1-methyl-1H-[1,2,3]triazole

The reaction mixture was splitted in 24 tubes of 1.00 g (8.32 mmol) each. A mixture of 1-ethynyl-4-fluorobenzene (24.0 g, 200 mmol), sodium azide (14.41 g, 222 mmol), iodomethane (14.93 mL, 240 mmol), copper(I) iodide (8.03 g, 42 mmol) and L-(+)-ascorbic acid sodium salt (7.84 g, 40 mmol) in water (240 mL) was heated at 75° C. for 10 h. The mixture was then diluted with dichloromethane (25 mL) and filtered off. The aqueous layer of the filtrate was extracted with dichloromethane and the combined organic extracts washed with brine, dried over sodium sulphate, filtered and evaporated. Purification by chromatography (silica, 0 to 5% methanol in dichloromethane) afforded the title compound (20.3 g, 57%) as a white solid after recrystallisation from ethyl acetate-heptane. MS: m/e=178.1 [M+H]+.

b) 1-[5-(4-Fluoro-phenyl)-3-methyl-3H-[1,2,3]-triazol-4-yl]-ethanone

To a suspension of 4-(4-fluoro-phenyl)-1-methyl-1H-[1,2,3]triazole (3.54 g, 20.0 mmol) in DME (52 mL) was added n-BuLi (1.6 M in hexane, 15.0 mL, 24.0 mmol) dropwise at −75° C. The mixture was allowed to warm up to −35° C. and was stirred at −35° C. for 1 h. The reaction mixture was cooled again to −78° C. and a light green suspension of CuCN (1.79 g, 20.0 mmol) and LiCl (1.70 g, 40.0 mmol) in THF (26 ml) was added rapidly while stirring at −78° C. After 1 h the mixture was allowed to warm up to −35° C. and acetyl chloride (7.10 mL, 100.0 mmol) was added dropwise at this temperature. Then the reaction mixture was stirred at room temperature for 2 h and then poured carefully into aqueous saturated sodium carbonate solution (150 mL) and extracted with ethyl acetate. The combined organic extracts were washed with brine, dried over sodium sulphate, filtered and evaporated. Purification by chromatography (silica, 0 to 100% ethyl acetate in heptane) afforded the title compound (2.2 g, 50%) as a yellow oil. MS: m/e=220.3 [M+H]+.

c) 2-Bromo-1-[5-(4-fluoro-phenyl)-3-methyl-3H-[1,2,3]-triazol-4-yl]-ethanone

A solution of 1-[5-(4-fluoro-phenyl)-3-methyl-3H-[1,2,3]triazol-4-yl]-ethanone (4.02 g, 18.34 mmol) was dissolved in chloroform (18 mL) and acetic (0.36 mL) was heated to reflux and then a solution of bromine (1.04 mL, 20.17 mmol) in chloroform (9 mL) was added dropwise within 10 min at and after 1 h bromine (0.10 mL, 2.02 mmol) was added and heated under reflux for 1 h. After cooling to room temperature the mixture was poured onto ice-water and the mixture extracted with dichloromethane. The combined organic extracts were washed with water, brine, dried over sodium sulphate, filtered and evaporated. Purification by chromatography (silica, 0 to 100% ethyl acetate in heptane) afforded the title compound (3.48 g, 63%) as a light red solid. MS: m/e=298.1/300.1 [M+H]+.

d) 4-(4-Fluoro-phenyl)-5-(1H-imidazol-4-yl)-1H-[1,2,3]triazole

A suspension of 2-bromo-1-[5-(4-fluoro-phenyl)-3-methyl-3H-[1,2,3]triazol-4-yl]-ethanone (3.44 g, 11.54 mmol) in formamide (11.04 mL, 276.94 mmol) and water (1.25 mL, 69.24 mmol) was heated in the microwave to 140° C. for 3 h. After cooling to room temperature the mixture was poured into HCl (1 N, 150 mL) and the mixture extracted with ethyl acetate. The aqueous phase was made alkaline with NaOH (6 N) and then extracted twice with ethyl acetate and the combined extracts washed with water, brine, dried over sodium sulphate, filtered and evaporated. Purification by triturating (ethyl acetate) afforded the title compound (1.29 g, 46%) as a light brown solid. MS: m/e=244.2 [M+H]+.

e) 1-(4-{4-[5-(4-Fluoro-phenyl)-3-methyl-3H-[1,2,3]triazol-4-yl]-imidazol-1-yl}-phenyl)-ethanone A mixture of 4-(4-fluoro-phenyl)-5-(1H-imidazol-4-yl)-1-methyl-1H-[1,2,3]triazole (73 mg, 0.30 mmol), 4-fluoroacetophenone (37 µL, 0.30 mmol) and potassium carbonate (83 mg, 0.60 mmol) in DMF (1.5 mL) was stirred under Ar in a sealed flask and heated at 120° C. for 16 h. After cooling to room temperature the mixture was poured into water and extracted with ethyl acetate and the combined extracts washed with water, brine, dried over sodium sulphate, filtered and evaporated. Purification by chromatography (silica, 0 to 100% ethyl acetate in heptane) afforded the title compound (51 mg, 47%) as an off white solid after recrystallisation from ethyl acetate. MS: m/e=362.2 [M+H]+.

Example 2

4-{4-[5-(4-Fluoro-phenyl)-3-methyl-3H-[1,2,3]triazol-4-yl]-imidazol-1-yl}-benzoic acid methyl ester

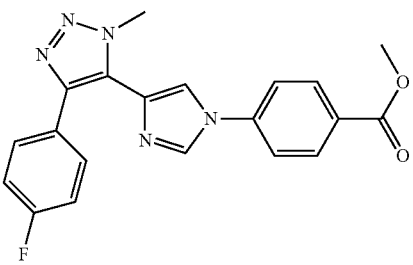 [SMILES: COC(=O)c1ccc(-n2cnc(-c3c(-c4ccc(F)cc4)nnn3C)c2)cc1]

A mixture of 4-(4-fluoro-phenyl)-5-(1H-imidazol-4-yl)-1-methyl-1H-[1,2,3]triazole (486 mg, 2.00 mmol), methyl 4-fluorobenzoate (308 mg, 2.00 mmol) and potassium carbonate (553 mg, 4.00 mmol) in DMF (10 mL) was stirred under Ar in a sealed flask and heated at 120° C. for 16 h. After cooling to room temperature the mixture was poured into water and extracted with ethyl acetate and the combined extracts washed with water, brine, dried over sodium sulphate, filtered and evaporated. Purification by chromatography (silica, 0 to 100% ethyl acetate in heptane) afforded the title compound (399 mg, 53%) as a white solid. MS: m/e=378.4 [M+H]⁺.

Example 3

4-{4-[5-(4-Fluoro-phenyl)-3-methyl-3H-[1,2,3]triazol-4-yl]-imidazol-1-yl}-N-isopropyl-benzamide

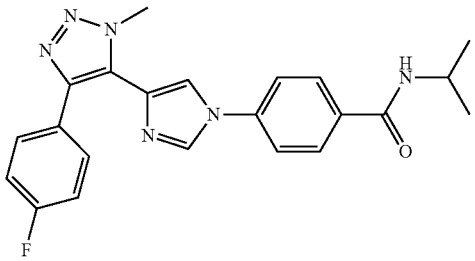 [SMILES: CC(C)NC(=O)c1ccc(-n2cnc(-c3c(-c4ccc(F)cc4)nnn3C)c2)cc1]

a) 4-{4-[5-(4-Fluoro-phenyl)-3-methyl-3H-[1,2,3]triazol-4-yl]-imidazol-1-yl}-benzoic acid A solution of lithium hydroxide monohydrate (85 mg, 2.01 mmol) in water (2.5 mL) was added dropwise to a suspension of 4-{4-[5-(4-fluoro-phenyl)-3-methyl-3H-[1,2,3]triazol-4-yl]-imidazol-1-yl}-benzoic acid methyl ester (380 mg, 1.01 mmol) in THF (2.5 mL) and methanol (0.5 mL). The reaction mixture was then stirred at room temperature for 1 h and was then evaporated and the residue dissolved in water, acidified with HCl (1 N), and the resulting precipitate filtered off to afford the title product (315 mg, 86%) as a white solid. MS: m/e=362.3 [M–H]⁻.

b) 4-{4-[5-(4-Fluoro-phenyl)-3-methyl-3H-[1,2,3]triazol-4-yl]-imidazol-1-yl}-N-isopropyl-benzamide To a solution of 4-{4-[5-(4-fluoro-phenyl)-3-methyl-3H-[1,2,3]triazol-4-yl]-imidazol-1-yl}-benzoic acid (75 mg, 0.21 mmol) and TBTU (73 mg, 0.23 mmol) in DMF (0.8 mL) was added DIPEA (177 μL, 1.03 mmol). Then isopropylamine (19 μL, 0.23 mmol) was added and the mixture was stirred at room temperature under Ar for 1 h. The mixture was then evaporated and purification by chromatography (silica, 0 to 100% ethyl acetate in heptane, then 0 to 10% methanol in dichloromethane) afforded the title compound (57 mg, 68%) as a white solid. MS: m/e=405.4 [M+H]⁺.

Example 4

4-{4-[5-(4-Fluoro-phenyl)-3-methyl-3H-[1,2,3]triazol-4-yl]-imidazol-1-yl}-N-(tetrahydropyran-4-yl)-benzamide

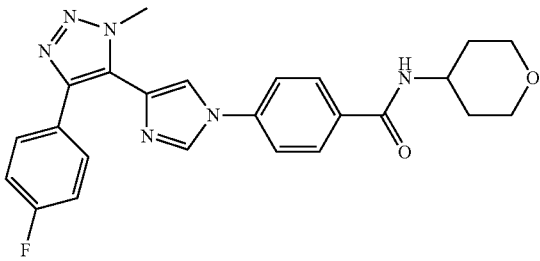 [SMILES: Cn1nnc(-c2ccc(F)cc2)c1-c1cn(-c2ccc(C(=O)NC3CCOCC3)cc2)cn1]

As described for example 3b, 4-{4-[5-(4-fluoro-phenyl)-3-methyl-3H-[1,2,3]triazol-4-yl]-imidazol-1-yl}-benzoic acid (75 mg, 0.21 mmol) was converted, using 4-aminotetrahydropyran instead of isopropylamine, to the title compound (73 mg, 79%) which was obtained as a white solid. MS: m/e=447.3 [M+H]⁺.

Example 5

4-{4-[5-(4-Fluoro-phenyl)-3-methyl-3H-[1,2,3]triazol-4-yl]-imidazol-1-yl}-N-(3-methyl-oxetan-3-yl)-benzamide

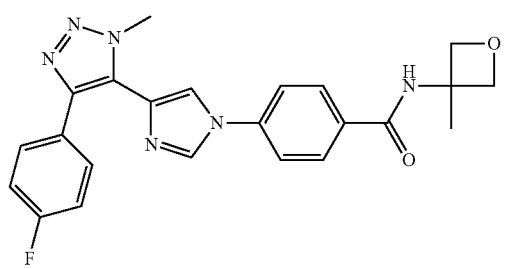 [SMILES: Cn1nnc(-c2ccc(F)cc2)c1-c1cn(-c2ccc(C(=O)NC3(C)COC3)cc2)cn1]

As described for example 3b, 4-{4-[5-(4-fluoro-phenyl)-3-methyl-3H-[1,2,3]triazol-4-yl]-imidazol-1-yl}-benzoic acid (75 mg, 0.21 mmol) was converted, using 3-methyl-3-oxetanamine instead of isopropylamine, to the title compound (57 mg, 64%) which was obtained as a white solid after trituration from ethyl acetate. MS: m/e=433.4 [M+H]⁺.

Example 6

(4-{4-[5-(4-Fluoro-phenyl)-3-methyl-3H-[1,2,3]triazol-4-yl]-imidazol-1-yl}-phenyl)-(2-oxa-6-aza-spiro[3.3]hept-6-yl)-methanone

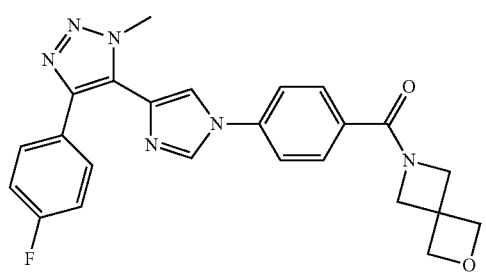 [SMILES: Cn1nnc(-c2ccc(F)cc2)c1-c1cn(-c2ccc(C(=O)N3CC4(COC4)C3)cc2)cn1]

As described for example 3b, 4-{4-[5-(4-fluoro-phenyl)-3-methyl-3H-[1,2,3]triazol-4-yl]-imidazol-1-yl}-benzoic acid (75 mg, 0.21 mmol) was converted, using 2-oxa-6-azonia-spiro[3.3]heptane oxalate salt instead of isopropylamine, to the title compound (53 mg, 58%) which was obtained as a white solid after trituration from ethyl acetate. MS: m/e=445.4 [M+H]⁺.

Example 7

4-{4-[5-(4-Fluoro-phenyl)-3-methyl-3H-[1,2,3]triazol-4-yl]-imidazol-1-yl}-benzamide

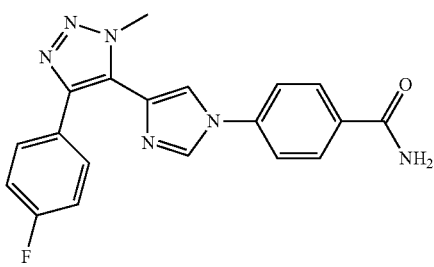 [SMILES: Cn1nnc(-c2ccc(F)cc2)c1-c1cn(-c2ccc(C(N)=O)cc2)cn1]

To a solution of 4-{4-[5-(4-fluoro-phenyl)-3-methyl-3H-[1,2,3]triazol-4-yl]-imidazol-1-yl}-benzoic acid (76 mg, 0.209 mmol) in DMF (2 mL) was added CDI (41 mg, 0.251 mmol) and the resulting mixture stirred at 60° C. for 1 h. After cooling to room temperature ammonium hydroxide (330 µL, 2.09 mmol) was added and reaction mixture was stirred for 1 h and then evaporated. Purification by crystallization afforded the title compound (64 mg, 84%) as a white solid. MS: m/e=363.2 [M+H]$^+$.

Example 8

4-(2-Fluorophenyl)-1-methyl-5-(1-(4-(trifluoromethyl)phenyl)-1H-imidazol-4-yl)-1H-1,2,3-triazole

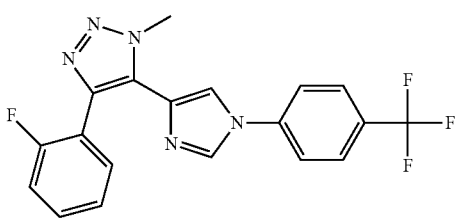 [SMILES: Cn1nnc(-c2ccccc2F)c1-c1cn(-c2ccc(C(F)(F)F)cc2)cn1]

a) 4-(2-Fluorophenyl)-1-methyl-1H-1,2,3-triazole

Solution A was composed of 1-ethynyl-2-fluorobenzene (4.2 g, 35 mmol) and iodomethane (5.96 g, 42 mmol) in acetonitrile (94 mL) and Solution B was composed of sodium azide (2.73 g, 42 mmol) and copper(I) iodide (1.33 g, 6.99 mmol) in water (100 mL). The reaction was ran in Uniqsis FlowSyn apparatus at 150° C. at 100 psi with flow rate of 1.0 mL/min and residence time of 1.5 min for each solution A and B. The reaction flow eluent was collected in an aqueous ammonium hydroxide solution (25%) and the mixture extracted with ethyl acetate. The combined organic extracts were washed with brine, dried over sodium sulphate, filtered and evaporated. Purification by chromatography (silica, 10 to 60% ethyl acetate in heptane) afforded the title compound (1.5 g, 24%) as a light yellow solid. MS: m/e=178.3 [M+H]$^+$.

b) 1-(4-(2-Fluorophenyl)-1-methyl-1H-1,2,3-triazol-5-yl)ethanone

As described for example 1b, 4-(2-fluorophenyl)-1-methyl-1H-1,2,3-triazole (5.0 g, 28.2 mmol) instead of 4-(4-fluoro-phenyl)-1-methyl-1H-[1,2,3]triazole, was converted to the title compound (3.33 g, 54%) which was obtained as a colorless liquid after purification by chromatography (silica, 0 to 50% ethyl acetate in heptane). MS: m/e=220.2 [M+H]$^+$.

c) 2-Bromo-1-(4-(2-fluorophenyl)-1-methyl-1H-1,2,3-triazol-5-yl)ethanone

As described for example 1c, 1-(4-(2-fluorophenyl)-1-methyl-1H-1,2,3-triazol-5-yl)ethanone (2.1 g, 9.58 mmol) instead of 1-[5-(4-fluoro-phenyl)-3-methyl-3H-[1,2,3]triazol-4-yl]-ethanone, was converted to the title compound (2.01 g, 70%) which was obtained as an off white solid after purification by chromatography (silica, 10 to 60% ethyl acetate in heptane). MS: m/e=378.0/380.0 [M+H]$^+$.

d) 4-(2-Fluorophenyl)-5-(1H-imidazol-4-yl)-1-methyl-1H-1,2,3-triazole

As described for example 1d, 2-bromo-1-(4-(2-fluorophenyl)-1-methyl-1H-1,2,3-triazol-5-yl)ethanone (1.0 g, 3.35 mmol) instead of 2-bromo-1-[5-(4-fluoro-phenyl)-3-methyl-3H-[1,2,3]triazol-4-yl]-ethanone, was converted to the title compound (814 mg, 49%) which was obtained as a white solid after purification by chromatography (silica, ethyl acetate). MS: m/e=244.2 [M+H]$^+$.

e) 4-(2-Fluorophenyl)-1-methyl-5-(1-(4-(trifluoromethyl)phenyl)-1H-imidazol-4-yl)-1H-1,2,3-triazole A mixture of 4-(2-fluorophenyl)-5-(1H-imidazol-4-yl)-1-methyl-1H-1,2,3-triazole (70 mg, 0.29 mmol), 4-fluorobenzotrifluoride (73 µL, 0.58 mmol) and potassium carbonate (80 mg, 0.58 mmol) in DMF (2.0 mL) was stirred under Ar in a sealed flask and heated at 120° C. for 16 h. After cooling to room temperature the mixture was poured into water and extracted with ethyl acetate and the combined extracts washed with water, brine, dried over sodium sulphate, filtered and evaporated. Purification by chromatography (silica, 0 to 5% methanol in dichloromethane) afforded the title compound (87 mg, 78%) as an off white solid. MS: m/e=388.2 [M+H]$^+$.

Example 9

4-(2-Fluorophenyl)-1-methyl-5-(1-(4-nitrophenyl)-1H-imidazol-4-yl)-1H-1,2,3-triazole

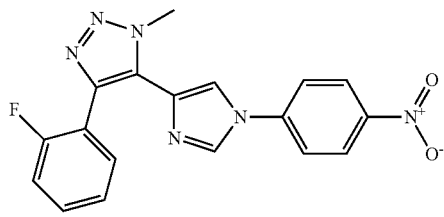 [SMILES: Cn1nnc(-c2ccccc2F)c1-c1cn(-c2ccc([N+](=O)[O-])cc2)cn1]

As described for example 8e, 4-(2-fluorophenyl)-5-(1H-imidazol-4-yl)-1-methyl-1H-1,2,3-triazole (70 mg, 0.29 mmol), was converted, using 1-fluoro-4-nitrobenzene instead of 4-fluorobenzotrifluoride, to the title compound (100 mg, 95%) which was obtained as a yellow solid. MS: m/e=365.1 [M+H]$^+$.

Example 10

1-(4-(4-(4-(2-Fluorophenyl)-1-methyl-1H-1,2,3-triazol-5-yl)-1H-imidazol-1-yl)phenyl)ethanone

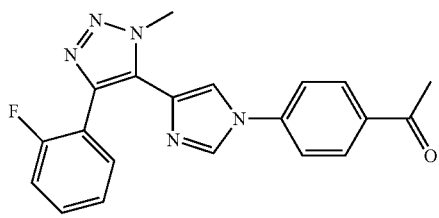 [SMILES: CC(=O)c1ccc(-n2cnc(-c3c(-c4ccccc4F)nnn3C)c2)cc1]

As described for example 8e, 4-(2-fluorophenyl)-5-(1H-imidazol-4-yl)-1-methyl-1H-1,2,3-triazole (70 mg, 0.29 mmol), was converted, using 4'-fluoro-acetophenone instead of 4-fluorobenzotrifluoride, to the title compound (85 mg, 82%) which was obtained as an off white solid. MS: m/e=362.2 [M+H]$^+$.

Example 11

6-{4-[5-(4-Fluoro-phenyl)-3-methyl-3H-[1,2,3]triazol-4-yl]-imidazol-1-yl}-N-isopropyl-nicotinamide

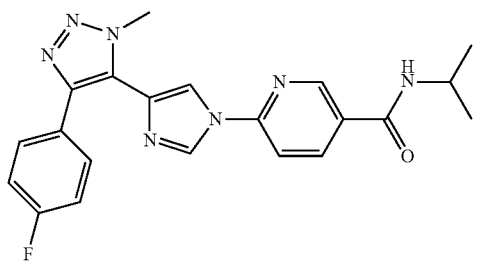

a) 6-{4-[5-(4-Fluoro-phenyl)-3-methyl-3H-[1,2,3]triazol-4-yl]-imidazol-1-yl}-nicotinic acid methyl ester A mixture of 4-(4-fluoro-phenyl)-5-(1H-imidazol-4-yl)-1-methyl-1H-[1,2,3]triazole (82 mg, 0.34 mmol), methyl 6-chloronicotinate (58 mg, 0.34 mmol) and potassium carbonate (93 mg, 0.67 mmol) in DMF (1.7 mL) was stirred under Ar in a sealed flask and heated at 120° C. for 16 h. After cooling to room temperature the mixture was poured into HCl (1 N) and extracted with ethyl acetate and the combined extracts washed with water, brine, dried over sodium sulphate, filtered and evaporated. Purification by chromatography (silica, 0 to 100% ethyl acetate in heptane) afforded the title compound (70 mg, 55%) as an off white solid. MS: m/e=379.2 [M+H]$^+$.

b) 6-[5-(4-Fluoro-phenyl)-3-methyl-3H-[1,2,3]-triazol-4-ylmethoxy]-nicotinic acid A solution of lithium hydroxide monohydrate (85 mg, 2.01 mmol) in water (2.5 mL) was added dropwise to a suspension of 6-{4-[5-(4-fluoro-phenyl)-3-methyl-3H-[1,2,3]triazol-4-yl]-imidazol-1-yl}-nicotinic acid methyl ester (381 mg, 1.01 mmol) in THF (2.5 mL). The reaction mixture was then stirred at room temperature for 1 h and was then evaporated and the residue dissolved in water, acidified with HCl (1 N), and the resulting precipitate filtered off to afford the title product (349 mg, 95%) as an off white solid. MS: m/e=363.3 [M−H]$^-$.

c) 6-{4-[5-(4-Fluoro-phenyl)-3-methyl-3H-[1,2,3]-triazol-4-yl]-imidazol-1-yl}-N-isopropyl-nicotinamide To a solution of 6-[5-(4-fluoro-phenyl)-3-methyl-3H-[1,2,3]triazol-4-ylmethoxy]-nicotinic acid (30 mg, 0.08 mmol) and TBTU (29 mg, 0.09 mmol) in DMF (0.2 mL) was added DIPEA (70 µL, 0.41 mmol). Then isopropylamine (8 µL, 0.09 mmol) was added and the mixture was stirred at room temperature under Ar for 1 h. The mixture was then evaporated and purification by chromatography (silica, 0 to 100% ethyl acetate in heptane) afforded the title compound (19 mg, 97%) as a white solid. MS: m/e=406.4 [M+H]$^+$.

Example 12

6-{4-[5-(4-Fluoro-phenyl)-3-methyl-3H-[1,2,3]triazol-4-yl]-imidazol-1-yl}-N-(tetrahydropyran-4-yl)-nicotinamide

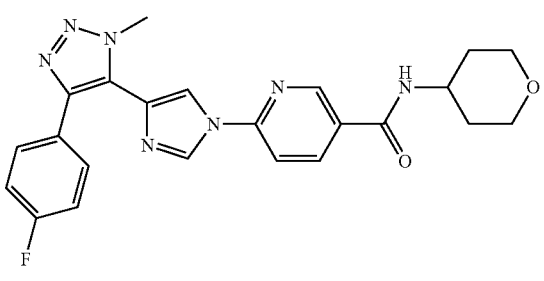 [SMILES: Cn1nnc(-c2ccc(F)cc2)c1-c1cn(-c2ccc(C(=O)NC3CCOCC3)cn2)cn1]

As described for example 11c, 6-[5-(4-fluoro-phenyl)-3-methyl-3H-[1,2,3]triazol-4-ylmethoxy]-nicotinic acid (109 mg, 0.30 mmol) was converted, using 4-aminotetrahydropyran instead of isopropylamine, to the title compound (70 mg, 52%) which was obtained as a white solid after trituration from methanol water. MS: m/e=448.2 [M+H]$^+$.

Example 13

6-{4-[5-(4-Fluoro-phenyl)-3-methyl-3H-[1,2,3]triazol-4-yl]-imidazol-1-yl}-N-(3-methyl-oxetan-3-yl)-nicotinamide

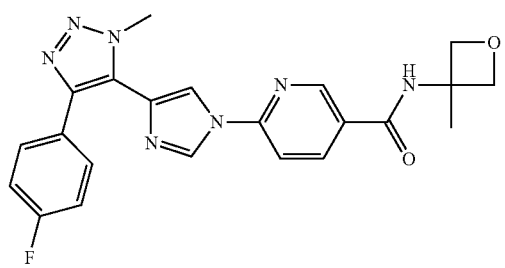 [SMILES: Cn1nnc(-c2ccc(F)cc2)c1-c1cn(-c2ccc(C(=O)NC3(C)COC3)cn2)cn1]

As described for example 11c, 6-[5-(4-fluoro-phenyl)-3-methyl-3H-[1,2,3]triazol-4-ylmethoxy]-nicotinic acid (109 mg, 0.30 mmol) was converted, using 3-methyl-3-oxetanamine instead of isopropylamine, to the title compound (66 mg, 51%) which was obtained as an off white solid after recrystallisation from ethyl acetate-heptane. MS: m/e=434.3 [M+H]$^+$.

Example 14

(6-{4-[5-(4-Fluoro-phenyl)-3-methyl-3H-[1,2,3]triazol-4-yl]-imidazol-1-yl}-pyridin-3-yl)-(2-oxa-6-aza-spiro[3.3]hept-6-yl)-methanone

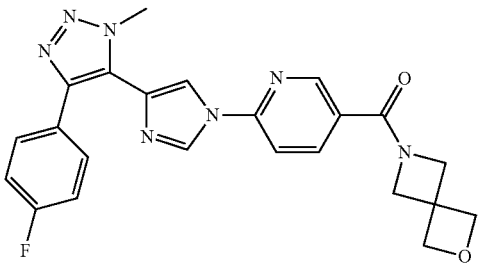

As described for example 11c, 6-[5-(4-fluoro-phenyl)-3-methyl-3H-[1,2,3]triazol-4-ylmethoxy]-nicotinic acid (109 mg, 0.30 mmol) was converted, using 2-oxa-6-azonia-spiro[3.3]heptane oxalate salt instead of isopropylamine, to the title compound (55 mg, 41%) which was obtained as a light yellow solid. MS: m/e=446.2 [M+H]$^+$.

Example 15

2-{4-[5-(4-Fluoro-phenyl)-3-methyl-3H-[1,2,3]triazol-4-yl]-imidazol-1-yl}-5-trifluoromethyl-pyridine

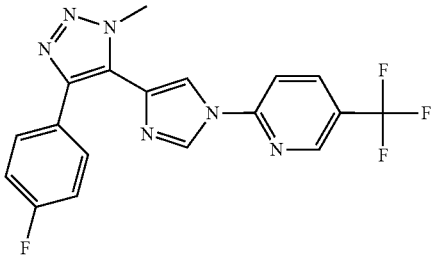 [SMILES: Cn1nnc(-c2ccc(F)cc2)c1-c1cn(-c2ccc(C(F)(F)F)cn2)cn1]

A mixture of 4-(4-fluoro-phenyl)-5-(1H-imidazol-4-yl)-1-methyl-1H-[1,2,3]triazole (36 mg, 0.15 mmol), 2-chloro-5-(trifluoromethyl)pyridine (27 mg, 0.15 mmol) and potassium carbonate (41 mg, 0.3 mmol) in DMF (0.6 mL) was stirred under Ar in a sealed flask and heated at 120° C. for 16 h. After cooling to room temperature the mixture was poured into water and extracted with ethyl acetate and the combined extracts washed with water, brine, dried over sodium sulphate, filtered and evaporated. Purification by chromatography (silica, 0 to 100% ethyl acetate in heptane) afforded the title compound (48 mg, 84%) as a white solid. MS: m/e=389.2 [M+H]$^+$.

Example 16

6-(4-(4-(4-Fluorophenyl)-1-methyl-1H-1,2,3-triazol-5-yl)-1H-imidazol-1-yl)nicotinamide

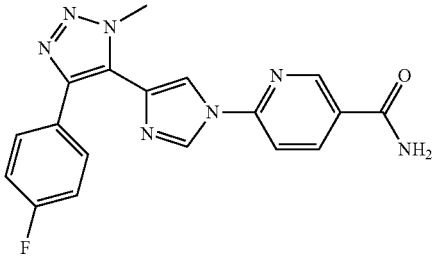 [SMILES: Cn1nnc(-c2ccc(F)cc2)c1-c1cn(-c2ccc(C(N)=O)cn2)cn1]

To a solution of 6-[5-(4-fluoro-phenyl)-3-methyl-3H-[1,2,3]triazol-4-ylmethoxy]-nicotinic acid (100 mg, 0.274 mmol) in DMF (3 mL) was added CDI (54 mg, 0.329 mmol) and the resulting mixture stirred at 60° C. for 1 h. After cooling to room temperature ammonium hydroxide (430 µL, 2.74 mmol) was added and reaction mixture was stirred for 1 h and then evaporated. Purification by chromatography (silica, 0 to 5% methanol in dichloromethane) afforded the title compound (64 mg, 64%) as a white solid. MS: m/e=364.1 [M+H]$^+$.

Example 17

Methyl 6-(4-(4-(2-chlorophenyl)-1-methyl-1H-1,2,3-triazol-5-yl)-1H-imidazol-1-yl)nicotinate

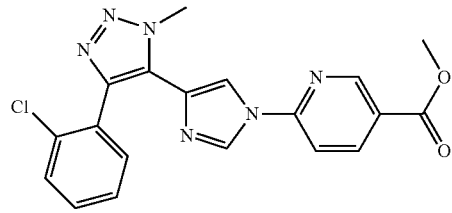 [SMILES: COC(=O)c1ccc(-n2cnc(-c3c(-c4ccccc4Cl)nnn3C)c2)nc1]

a) 4-(2-Chlorophenol)-1-methyl-1H-1,2,3-triazole

Solution A was composed of 1-chloro-2-ethynylbenzene (6.69 g, 49 mmol) and iodomethane (8.35 g, 58.8 mmol) in acetonitrile (40.4 mL) and Solution B was composed of L-(+)-ascorbic acid sodium salt (1.73 g, 9.8 mmol) and sodium azide (3.5 g, 53.9 mmol) in water (50 mL), water:acetonitrile (1:1, 100 mL). Copper(I) iodide was supported on a bed of molecular sieves and decalite filter. The reaction was ran in Uniqsis FlowSyn apparatus at 120° C. at 100 psi with flow rate of 0.25 mL/min and residence time of 4 min for each solution A and B. The reaction flow eluent was collected in an aqueous ammonium hydroxide solution (25%) and the mixture extracted with ethyl acetate. The combined organic extracts were washed with brine, dried over sodium sulphate, filtered and evaporated. Purification by chromatography (silica, 10 to 60% ethyl acetate in heptane) afforded the title compound (2.4 g, 25%) as a light brown solid. MS: m/e=194.1 [M+H]$^+$.

b) 1-(4-(2-Chlorophenol)-1-methyl-1H-1,2,3-triazol-5-yl)ethanone

To a suspension of 4-(2-chlorophenyl)-1-methyl-1H-1,2,3-triazole (2.0 g, 10.3 mmol) in DME (30 mL) was added n-BuLi (1.6 M in hexane, 7.75 mL, 12.4 mmol) dropwise at −75° C. The mixture was allowed to warm up to −35° C. and was stirred at −35° C. for 1 h. The reaction mixture was cooled again to −78° C. and a light green suspension of CuCN (925 mg, 10.3 mmol) and LiCl (876 mg, 20.7 mmol) in THF (15 ml) was added rapidly while stirring at −78° C. After 1 h the mixture was allowed to warm up to −35° C. and acetyl chloride (3.67 mL, 51.6 mmol) was added dropwise at this temperature. Then the reaction mixture was stirred at room temperature for 3 h and then poured carefully into aqueous saturated sodium carbonate solution (75 mL) and extracted with ethyl acetate. The combined organic extracts were washed with brine, dried over sodium sulphate, filtered and evaporated. Purification by chromatography (silica, 10 to 60% ethyl acetate in heptane) afforded the title compound (1.06 g, 44%) as a yellow oil. MS: m/e=236.1 [M+H]+.

c) 2-Bromo-1-(4-(2-chlorophenyl)-1-methyl-1H-1,2,3-triazol-5-yl)ethanone

A solution of 1-(4-(2-chlorophenyl)-1-methyl-1H-1,2,3-triazol-5-yl)ethanone (1.02 g, 4.33 mmol) was dissolved in chloroform (7 mL) and acetic (0.136 mL) was heated to reflux and then a solution of bromine (0.234 mL, 4.54 mmol) in chloroform (3 mL) was added dropwise within 10 min at and after 1 h bromine (0.09 mL, 1.73 mmol) in chloroform (2 mL) was added and heated under reflux for 1 h. After cooling to room temperature the mixture was poured onto ice-water and the mixture extracted with dichloromethane. The combined organic extracts were washed with water, brine, dried over sodium sulphate, filtered and evaporated. Purification by chromatography (silica, 10 to 60% ethyl acetate in heptane) afforded the title compound (988 mg, 73%) as an off white solid. MS: m/e=313.9/315.9 [M+H]+.

d) 4-(2-Chlorophenyl)-5-(1H-imidazol-4-yl)-1-methyl-1H-1,2,3-triazole

A suspension of 2-bromo-1-(4-(2-chlorophenyl)-1-methyl-1H-1,2,3-triazol-5-yl)ethanone (0.86 g, 2.73 mmol) in formamide (2.62 mL, 65.6 mmol) and water (0.296 mL, 16.4 mmol) was heated in the microwave to 140° C. for 3 h. After cooling to room temperature the mixture was poured into HCl (1 N, 20 mL) and the mixture extracted with ethyl acetate. The aqueous phase was made alkaline with NaOH (6 N) and then extracted twice with ethyl acetate and the combined extracts washed with water, brine, dried over sodium sulphate, filtered and evaporated. Purification by chromatography (silica, ethyl acetate) afforded the title compound (360 mg, 51%) as an off white solid. MS: m/e=260.0 [M+H]+.

e) Methyl 6-(4-(4-(2-chlorophenyl)-1-methyl-1H-1,2,3-triazol-5-yl)-1H-imidazol-1-yl)nicotinate A mixture of 4-(2-chlorophenyl)-5-(1H-imidazol-4-yl)-1-methyl-1H-1,2,3-triazole (322 mg, 1.24 mmol), methyl 6-chloronicotinate (213 mg, 1.24 mmol) and potassium carbonate (343 mg, 2.48 mmol) in DMF (7 mL) was stirred under Ar in a sealed flask and heated at 120° C. for 3 h. After cooling to room temperature the mixture was poured into water and extracted with ethyl acetate and the combined extracts washed with water, brine, dried over sodium sulphate, filtered and evaporated. Purification by chromatography (silica, 30 to 100% ethyl acetate in heptane) afforded the title compound (370 mg, 76%) as a white solid. MS: m/e=395.1 [M+H]+.

Example 18

6-(4-(4-(2-Chlorophenyl)-1-methyl-1H-1,2,3-triazol-5-yl)-1H-imidazol-1-yl)-N-isopropylnicotinamide

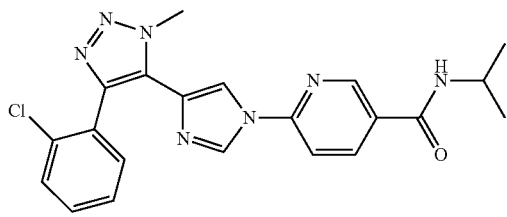 [SMILES: CC(C)NC(=O)c1ccc(-n2cnc(-c3c(-c4ccccc4Cl)nnn3C)c2)nc1]

a) 6-(4-(4-(2-Chlorophenyl)-1-methyl-1H-1,2,3-triazol-5-yl)-1H-imidazol-1-yl)nicotinic acid A solution of lithium hydroxide monohydrate (75 mg, 1.77 mmol) in water (3.5 mL) was added dropwise to a suspension of methyl 6-(4-(4-(2-chlorophenyl)-1H-methyl-1H-1,2,3-triazol-5-yl)-1H-imidazol-1-yl)nicotinate (349 mg, 0.884 mmol) in THF (7 mL) and methanol (1 mL). The reaction mixture was then stirred at room temperature for 1 h and was then evaporated and the residue dissolved in water, acidified with HCl (1 N), and the resulting precipitate filtered off to afford the title product (320 mg, 95%) as a white solid. MS: m/e=379.3 [M–H]−.

b) 6-(4-(4-(2-Chlorophenyl)-1-methyl-1H-1,2,3-triazol-5-yl)-1H-imidazol-1-yl)-N-isopropylnicotinamide To a solution of 6-(4-(4-(2-chlorophenyl)-1-methyl-1H-1,2,3-triazol-5-yl)-1H-imidazol-1-yl)nicotinic acid (74 mg, 0.194 mmol) and TBTU (69 mg, 0.214 mmol) in DMF (2.0 mL) was added DIPEA (170 μL, 0.972 mmol). Then isopropylamine (19 μL, 0.214 mmol) was added and the mixture was stirred at room temperature under Ar for 2 h. The mixture was then evaporated and purification by chromatography (silica, 50 to 100% ethyl acetate in heptane) afforded the title compound (52 mg, 63%) as a white solid. MS: m/e=422.1 [M+H]+.

Example 19

6-(4-(4-(2-Chlorophenyl)-1-methyl-1H-1,2,3-triazol-5-yl)-1H-imidazol-1-yl)nicotinamide

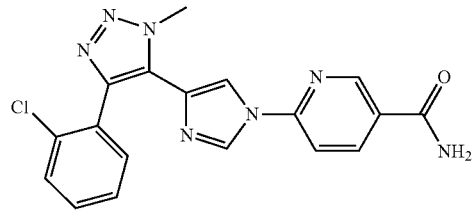 [SMILES: Cn1nnc(-c2ccccc2Cl)c1-c1cn(-c2ccc(C(N)=O)cn2)cn1]

To a solution of 6-(4-(4-(2-chlorophenyl)-1-methyl-1H-1,2,3-triazol-5-yl)-1H-imidazol-1-yl)nicotinic acid (74 mg, 0.194 mmol) in DMF (3 mL) was added CDI (38 mg, 0.233 mmol) and the resulting mixture stirred at 60° C. for 1 h. After cooling to room temperature ammonium hydroxide (305 μL, 1.94 mmol) was added and reaction mixture was stirred for 1 h and then evaporated. Purification by chromatography (reverse phase HPLC) afforded the title compound (54 mg, 73%) as a white foam. MS: m/e=380.1 [M+H]+.

Example 20

Methyl 6-(4-(4-(2-fluorophenyl)-1-methyl-1H-1,2,3-triazol-5-yl)-1H-imidazol-1-yl)nicotinate

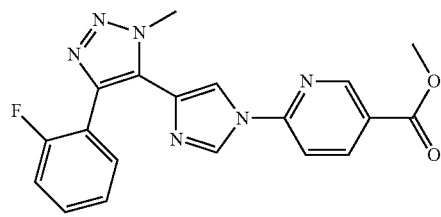 [SMILES: COC(=O)c1ccc(-n2cnc(-c3c(-c4ccccc4F)nnn3C)c2)nc1]

A mixture of 4-(2-fluorophenyl)-5-(1H-imidazol-4-yl)-1-methyl-1H-1,2,3-triazole (233 mg, 0.958 mmol), methyl 6-chloronicotinate (164 mg, 0.988 mmol) and potassium carbonate (265 mg, 1.92 mmol) in DMF (5.0 mL) was stirred under Ar in a sealed flask and heated at 120° C. for 3 h. After cooling to room temperature the mixture was poured into water and extracted with ethyl acetate and the combined extracts washed with water, brine, dried over sodium sulphate, filtered and evaporated. Purification by chromatography (silica, 50 to 100% ethyl acetate in heptane) afforded the title compound (303 mg, 79%) as a white solid. MS: m/e=379.2 [M+H]+.

Example 21

6-(4-(4-(2-Fluorophenyl)-1-methyl-1H-1,2,3-triazol-5-yl)-1H-imidazol-1-yl)nicotinic acid

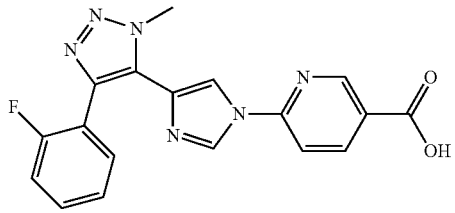 [SMILES: Cn1nnc(-c2ccccc2F)c1-c1cn(-c2ccc(C(=O)O)cn2)cn1]

A solution of lithium hydroxide monohydrate (63 mg, 1.49 mmol) in water (3.0 mL) was added dropwise to a suspension of methyl 6-(4-(4-(2-fluorophenyl)-1-methyl-1H-1,2,3-triazol-5-yl)-1H-imidazol-1-yl)nicotinate (282 mg, 0.745 mmol) in THF (6.0 mL) and methanol (1 mL). The reaction mixture was then stirred at room temperature for 1.5 h and was then evaporated and the residue dissolved in water, acidified with HCl (1 N), and the resulting precipitate filtered off to afford the title product (244 mg, 90%) as a white solid. MS: m/e=363.3 [M−H]−.

Example 22

6-(4-(4-(2-Fluorophenyl)-1-methyl-1H-1,2,3-triazol-5-yl)-1H-imidazol-1-yl)-N-(tetrahydro-2H-pyran-4-yl)nicotinamide

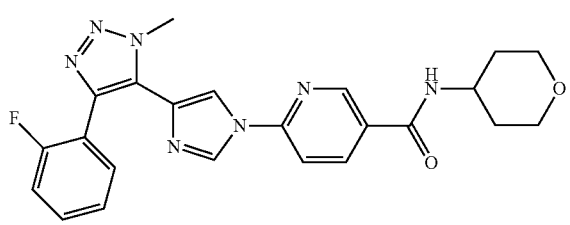 [SMILES: Cn1nnc(-c2ccccc2F)c1-c1cn(-c2ccc(C(=O)NC3CCOCC3)cn2)cn1]

To a solution of 6-(4-(4-(2-fluorophenyl)-1-methyl-1H-1,2,3-triazol-5-yl)-1H-imidazol-1-yl)nicotinic acid (75 mg, 0.194 mmol) and TBTU (73 mg, 0.226 mmol) in DMF (2.0 mL) was added DIPEA (180 μL, 1.03 mmol). Then 4-aminotetrahydropyran (24 μL, 0.226 mmol) was added and the mixture was stirred at room temperature under Ar for 30 min. The mixture was then evaporated and purification by chromatography (reverse phase HPLC) afforded the title compound (71 mg, 77%) as a white solid. MS: m/e=448.2 [M+H]+.

Example 23

6-(4-(4-(2-Fluorophenyl)-1-methyl-1H-1,2,3-triazol-5-yl)-1H-imidazol-1-yl)-N-isopropylnicotinamide

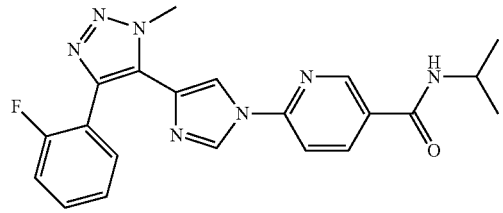 [SMILES: CC(C)NC(=O)c1ccc(-n2cnc(-c3c(-c4ccccc4F)nnn3C)c2)nc1]

As described for example 22, 6-(4-(4-(2-fluorophenyl)-1-methyl-1H-1,2,3-triazol-5-yl)-1H-imidazol-1-yl)nicotinic acid (75 mg, 0.194 mmol) was converted, using isopropylamine instead of 4-aminotetrahydropyran, to the title compound (51 mg, 61%) which was obtained as an off white foam. MS: m/e=406.3 [M+H]+.

Example 24

6-(4-(4-(2-Fluorophenyl)-1-methyl-1H-1,2,3-triazol-5-yl)-1H-imidazol-1-yl)-N-(2-hydroxy-2-methylpropyl)nicotinamide

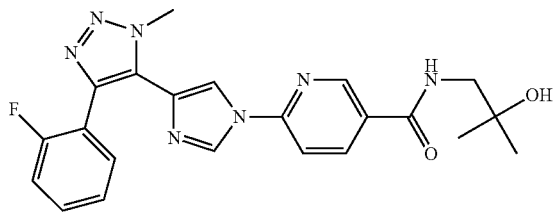 [SMILES: Cn1nnc(-c2ccccc2F)c1-c1cn(-c2ccc(C(=O)NCC(C)(C)O)cn2)cn1]

As described for example 22, 6-(4-(4-(2-fluorophenyl)-1-methyl-1H-1,2,3-triazol-5-yl)-1H-imidazol-1-yl)nicotinic acid (75 mg, 0.194 mmol) was converted, using 2-amino-2-methylpropan-1-ol instead of 4-aminotetrahydropyran, to the title compound (77 mg, 86%) which was obtained as an off white foam. MS: m/e=436.3 [M+H]+.

Example 25

6-(4-(4-(2-Fluorophenyl)-1-methyl-1H-1,2,3-triazol-5-yl)-1H-imidazol-1-yl)nicotinamide

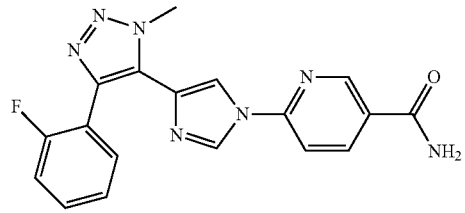 [SMILES: Cn1nnc(-c2ccccc2F)c1-c1cn(-c2ccc(C(N)=O)cn2)cn1]

To a solution of 6-(4-(4-(2-fluorophenyl)-1-methyl-1H-1,2,3-triazol-5-yl)-1H-imidazol-1-yl)nicotinic acid (69 mg, 0.189 mmol) in DMF (3 mL) was added CDI (37 mg, 0.227 mmol) and the resulting mixture stirred at 60° C. for 1 h. After cooling to room temperature ammonium hydroxide (300 μL, 1.9 mmol) was added and reaction mixture was stirred for 1 h and then evaporated. Purification by chromatography (reverse phase HPLC) afforded the title compound (56 mg, 81%) as a white foam. MS: m/e=364.1 [M+H]+.

Example 26

(6-(4-(4-(2-Fluorophenyl)-1-methyl-1H-1,2,3-triazol-5-yl)-1H-imidazol-1-yl)pyridin-3-yl)(2-oxa-6-azaspiro[3.3]heptan-6-yl)methanone

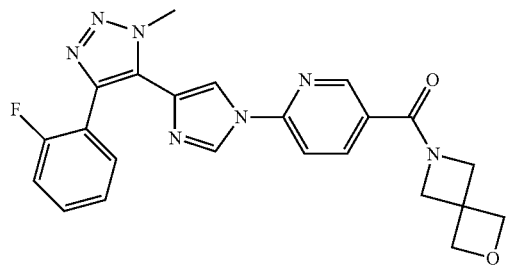 [SMILES: Cn1nnc(-c2ccccc2F)c1-c1cn(-c2ccc(C(=O)N3CC4(COC4)C3)cn2)cn1]

As described for example 22, 6-(4-(4-(2-fluorophenyl)-1-methyl-1H-1,2,3-triazol-5-yl)-1H-imidazol-1-yl)nicotinic acid (69 mg, 0.189 mmol) was converted, using 2-oxa-6-azonia-spiro[3.3]heptane oxalate salt instead of 4-aminotetrahydropyran, to the title compound (40 mg, 47%) which was obtained as an off white foam. MS: m/e=446.2 [M+H]+.

Example 27

6-(4-(4-(2-Fluorophenyl)-1-methyl-1H-1,2,3-triazol-5-yl)-1H-imidazol-1-yl)-N-(3-methyloxetan-3-yl)nicotinamide

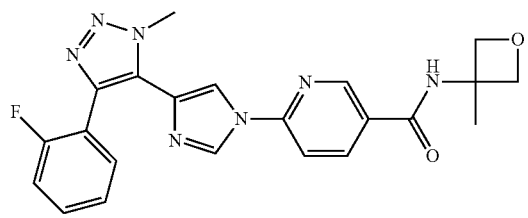 [SMILES: Cn1nnc(-c2ccccc2F)c1-c1cn(-c2ccc(C(=O)NC3(C)COC3)cn2)cn1]

As described for example 22, 6-(4-(4-(2-fluorophenyl)-1-methyl-1H-1,2,3-triazol-5-yl)-1H-imidazol-1-yl)nicotinic acid (69 mg, 0.189 mmol) was converted, using 3-methyl-3-oxetaneamine instead of 4-aminotetrahydropyran, to the title compound (61 mg, 74%) which was obtained as a white foam after purification by chromatography (silica, 0 to 10% methanol in dichloromethane). MS: m/e=434.3 [M+H]+.

Example 28

6-(4-(4-(2-Fluorophenyl)-1-methyl-1H-1,2,3-triazol-5-yl)-1H-imidazol-1-yl)-N-morpholinonicotinamide

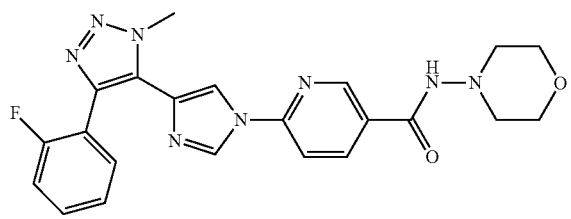

As described for example 22, 6-(4-(4-(2-fluorophenyl)-1-methyl-1H-1,2,3-triazol-5-yl)-1H-imidazol-1-yl)nicotinic acid (69 mg, 0.189 mmol) was converted, using 4-aminomorpholine instead of 4-aminotetrahydropyran, to the title compound (59 mg, 70%) which was obtained as a white foam after purification by chromatography (silica, 0 to 10% methanol in dichloromethane). MS: m/e=449.2 [M+H]+.

Example 29

N-Cyclopropyl-6-(4-(4-(2-fluorophenyl)-1-methyl-1H-1,2,3-triazol-5-yl)-1H-imidazol-1-yl)nicotinamide

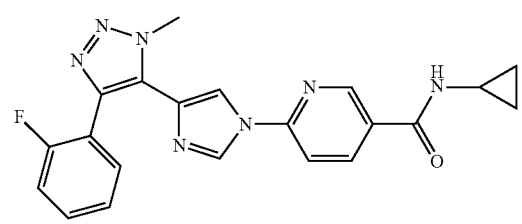 [SMILES: Cn1nnc(-c2ccccc2F)c1-c1cn(-c2ccc(C(=O)NC3CC3)cn2)cn1]

As described for example 22, 6-(4-(4-(2-fluorophenyl)-1-methyl-1H-1,2,3-triazol-5-yl)-1H-imidazol-1-yl)nicotinic acid (69 mg, 0.189 mmol) was converted, using cyclopropylamine instead of 4-aminotetrahydropyran, to the title compound (43 mg, 56%) which was obtained as a white foam. MS: m/e=404.4 [M+H]+.

Example 30

2-(4-(4-(2-Fluorophenyl)-1-methyl-1H-1,2,3-triazol-5-yl)-1H-imidazol-1-yl)-5-(trifluoromethyl)pyridine

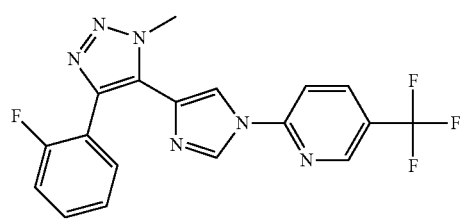 [SMILES: Cn1nnc(-c2ccccc2F)c1-c1cn(-c2ccc(C(F)(F)F)cn2)cn1]

A mixture of 4-(2-fluorophenyl)-5-(1H-imidazol-4-yl)-1-methyl-1H-1,2,3-triazole (70 mg, 0.288 mmol), 2-chloro-5-(trifluoromethyl)pyridine (53 mg, 0.288 mmol) and potassium carbonate (80 mg, 0.576 mmol) in DMF (2.0 mL) was stirred under Ar in a sealed flask and heated at 120° C. for 3 h. After cooling to room temperature the mixture was poured into water and extracted with ethyl acetate and the combined extracts washed with water, brine, dried over sodium sulphate, filtered and evaporated. Purification by chromatography (silica, 0 to 5% methanol in dichloromethane) afforded the title compound (85 mg, 76%) as an off white solid. MS: m/e=389.2 [M+H]+.

Example 31

1-(4-Fluoro-phenyl)-4-methyl-5-[1-(4-trifluorom-ethyl-phenyl)-1H-imidazol-4-yl]-1H-[1,2,3]triazole

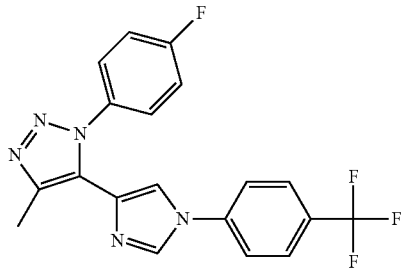 [SMILES: Cc1nnn(-c2ccc(F)cc2)c1-c1cn(-c2ccc(C(F)(F)F)cc2)cn1]

1-Azido-4-fluoro-benzene

Prepared in analogy to J. Org. Chem. (1989) 54:5938-5945. To a solution of sulfuric acid (40 mL) and trifluoroacetic acid (200 mL) was added 4-fluoroaniline (22.1 mL, 0.23 mol) dropwise. Then under ice-cooling a solution of sodium nitrite (20.6 g, 0.3 mol) in water (200 mL) was added over 30 min at 15-18° C. The solution was then stirred for 30 min while kept in the ice bath. A solution of sodium azide (25.42 g, 0.39 mol) in water (150 mL) was added dropwise over 30 min. Mixture was foaming and temperature went up to 10° C. while cooling with an ice bath. Reaction mixture was stirred without cooling for 1 h, then extracted with diethyl ether. The combined organic layers were washed with water two times. Then the combined organic layers were diluted with saturated aqueous sodium carbonate solution (500 mL) until the mixture became basic. The organic phase was separated and washed with brine, extracted again with diethyl ether. The organic layers were dried over sodium sulfate and evaporated at 40° C., minimum 50 mbar (already distillation of product), to afford the title product (30.42 g, 96%) as a brown liquid.

b) 1-[3-(4-Fluoro-phenyl)-5-methyl-4,5-dihydro-3H-[1,2,3]triazol-4-yl]-piperidine Prepared in analogy to EP 0 433 842 A2. A mixture of 1-azido-4-fluoro-benzene (2.80 g, 20 mmol) and 1-(1-propenyl)-piperidine (18%, 14.2 g, 20 mmol) was stirred under ice cooling (slowly exothermic in the beginning) and at room temperature for 144 h in the absence of light. Hexane was then added to the brown solutions and a solid formed which was filtered off, washed with hexane and dried in hv to give the title product (1.1 g) as a light pink solid. The filtrate was then evaporated and purification by chromatography (silica, 10 to 50% ethyl acetate in heptane) afforded the title compound (4.34 g) as a light yellow solid. Total yield (5.44 g, 98%). MS: m/e=263.1 [M+H]$^+$.

c) 1-(4-Fluoro-phenyl)-4-methyl-1H-[1,2,3]triazole

Prepared in analogy to EP 0 433 842 A2. A mixture of 1-[3-(4-fluoro-phenyl)-5-methyl-4,5-dihydro-3H-[1,2,3]triazol-4-yl]-piperidine (1.15 g, 0.004 mol) and potassium hydroxide in MeOH (2 N, 29.2 mL, 58 mmol) was heated under reflux for 6 h then cooled to room temperature. The mixture was then poured into water and extracted with diethyl ether and the combined organic extracts washed with brine, dried over sodium sulphate and evaporated to give the title product (555 mg) as a white solid. The filtrate was evaporated and purification by chromatography (silica, 10 to 60% ethyl acetate in heptane) afforded the title compound (41 mg, 79%) as an off white solid. Total yield (596 mg, 77%). MS: m/e=178.1 [M+H]$^+$.

d) 1-[3-(4-Fluoro-phenyl)-5-methyl-3H-[1,2,3]triazol-4-yl]-ethanone

To a suspension of 1-(4-fluoro-phenyl)-4-methyl-1H-[1,2,3]triazole (4.0 g, 23 mmol) in DME (114 mL) was added n-BuLi (1.6 M in hexane, 17.0 mL, 27 mmol) dropwise at −75° C. The mixture was allowed to warm up to −35° C. and was stirred at −35° C. for 1 h. The reaction mixture was cooled again to −78° C. and a light green suspension of CuCN (2.03 g, 23 mmol) and LiCl (1.92 g, 45 mmol) in THF (32 ml) was added rapidly while stirring at −78° C. After 1 h the mixture was allowed to warm up to −35° C. and acetyl chloride (8.02 mL, 113 mmol) was added dropwise at this temperature. Then the reaction mixture was stirred at room temperature for 2 h and then poured carefully into aqueous saturated sodium carbonate solution (160 mL) and extracted with ethyl acetate. The combined organic extracts were washed with brine, dried over sodium sulphate, filtered and evaporated. Purification by chromatography (silica, dichloromethane) afforded the title compound (3.63 g, 69%) as an off white solid. MS: m/e=220.3 [M+H]$^+$.

e) 2-Bromo-1-[3-(4-fluoro-phenyl)-5-methyl-3H-[1,2,3]triazol-4-yl]-ethanone

A solution of 1-[3-(4-fluoro-phenyl)-5-methyl-3H-[1,2,3]triazol-4-yl]-ethanone (3.62 g, 17 mmol) was dissolved in chloroform (28 mL) and acetic (0.5 mL) was heated to reflux and then a solution of bromine (0.89 mL, 17 mmol) in chloroform (9 mL) and heated under reflux for 2 h. After cooling to room temperature the mixture was poured onto ice-water and the mixture extracted with dichloromethane. The combined organic extracts were washed with water, brine, dried over sodium sulphate, filtered and evaporated. Purification by chromatography (silica, 10 to 60% ethyl acetate in heptane) afforded the title compound (3.34 g, 68%) as an off white solid. MS: m/e=298.3/300.2 [M+H]$^+$.

f) 1-(4-Fluoro-phenyl)-5-(1H-imidazol-4-yl)-4-methyl-1H-[1,2,3,]triazole

The reaction was conducted in triplicate. A suspension of 2-bromo-1-[3-(4-fluoro-phenyl)-5-methyl-3H-[1,2,3]triazol-4-yl]-ethanone (1.03 g, 3.0 mmol) in formamide (3.3 mL, 81 mmol) and water (0.37 mL, 20 mmol) was heated in the microwave to 140° C. for 3 h. After cooling to room temperature the 3 reaction mixtures were poured into HCl (1 N, 150 mL) and the mixture extracted with ethyl acetate. The aqueous phase was made alkaline with NaOH (6 N) and then extracted twice with ethyl acetate and the combined extracts washed with water, brine, dried over sodium sulphate, filtered and evaporated to afford the title compound (1.54 g, 62%) as a light brown solid. MS: m/e=244.3 [M+H]$^+$.

g) 1-(4-Fluoro-phenyl)-4-methyl-5-[1-(4-trifluorom-ethyl-phenyl)-1H-imidazol-4-yl]-1H-[1,2,3]-triazole A mixture of 1-(4-fluoro-phenyl)-5-(1H-imidazol-4-yl)-4-methyl-1H-[1,2,3]triazole (100 mg, 0.411 mmol), 4-fluorobenzotrifluoride (105 μL, 0.822 mmol) and potassium carbonate (114 mg, 0.82 mmol) in DMF (2.0 mL) was stirred under Ar in a sealed flask and heated at 120° C. for 48 h. After cooling to room temperature the mixture was poured into HCl (1 N) and extracted with ethyl acetate and the combined extracts washed with water, brine, dried over sodium sulphate, filtered and evaporated. Purification by chromatography (silica, 0 to 100% ethyl acetate in heptane) afforded the title compound (68 mg, 43%) as an off white solid. MS: m/e=388.2 [M+H]⁺.

Example 32

1-(4-{4-[3-(4-Fluoro-phenyl)-5-methyl-3H-[1,2,3]triazol-4-yl]-imidazol-1-yl}-phenyl)-ethanone

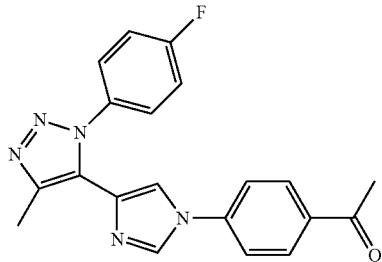 [SMILES: CC(=O)c1ccc(-n2cnc(-c3c(C)nnn3-c3ccc(F)cc3)c2)cc1]

A mixture of 1-(4-fluoro-phenyl)-5-(1H-imidazol-4-yl)-4-methyl-1H-[1,2,3]triazole (100 mg, 0.411 mmol), 4-fluoroacetophenone (51 μL, 0.411 mmol) and potassium carbonate (114 mg, 0.82 mmol) in DMF (2.0 mL) was stirred under Ar in a sealed flask and heated at 120° C. for 48 h. After cooling to room temperature the mixture was poured into HCl (1 N) and extracted with ethyl acetate and the combined extracts washed with water, brine, dried over sodium sulphate, filtered and evaporated. Purification by chromatography (silica, 0 to 100% ethyl acetate in heptane) afforded the title compound (79 mg, 53%) as an off white solid. MS: m/e=362.3 [M+H]⁺.

Example 33

Methyl 4-(4-(1-(2-fluorophenyl)-4-methyl-1H-1,2,3-triazol-5-yl)-1H-imidazol-1-yl)benzoate

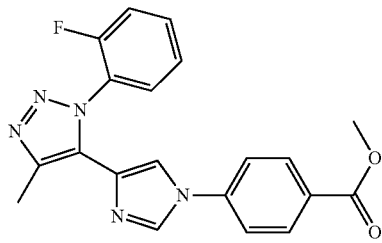 [SMILES: COC(=O)c1ccc(-n2cnc(-c3c(C)nnn3-c3ccccc3F)c2)cc1]

a) 1-Azido-2-fluorobenzene

As described for example 31a, 2-fluoroaniline (5.0 g, 45 mmol), instead of 4-fluoroaniline, was converted to the title compound (6.28 g, 99%) which was obtained as a brown liquid.

b) 1-(1-(2-Fluorophenyl)-4-methyl-4,5-dihydro-1H-1,2,3-triazol-5-yl)piperidine

As described for example 31b, 1-azido-2-fluorobenzene (2.8 g, 20 mmol), instead of 1-azido-4-fluoro-benzene, was converted to the title compound (4.87 g, 93%) which was obtained as a brown solid. MS: m/e=263.2 [M+H]⁺.

c) 1-(2-Fluorophenyl)-4-methyl-1H-1,2,3-triazole

As described for example 31c, 1-(1-(2-fluorophenyl)-4-methyl-4,5-dihydro-1H-1,2,3-triazol-5-yl)piperidine (1.32 g, 5.32 mmol), instead of 1-[3-(4-fluoro-phenyl)-5-methyl-4,5-dihydro-3H-[1,2,3]triazol-4-yl]-piperidine, was converted to the title compound (616 mg, 65%) which was obtained as a colorless liquid. MS: m/e=178.1 [M+H]⁺.

d) 1-(1-(2-Fluorophenyl)-4-methyl-1H-1,2,3-triazol-5-yl)ethanone

To a suspension of 1-(2-fluorophenyl)-4-methyl-1H-1,2,3-triazole (2.43 g, 13.7 mmol) in DME (40 mL) was added n-BuLi (1.6 M in hexane, 10.3 mL, 16.5 mmol) dropwise at −75° C. The mixture was allowed to warm up to −35° C. and was stirred at −35° C. for 1 h. The reaction mixture was cooled again to −78° C. and a light green suspension of CuCN (1.23 g, 13.7 mmol) and LiCl (1.16 g, 27.4 mmol) in THF (20 mL) was added rapidly while stirring at −78° C. After 1 h the mixture was allowed to warm up to −35° C. and acetyl chloride (4.88 mL, 68.6 mmol) was added dropwise at this temperature. Then the reaction mixture was stirred at room temperature for 2 h and then poured carefully into aqueous saturated sodium carbonate solution (100 mL) and extracted with ethyl acetate. The combined organic extracts were washed with brine, dried over sodium sulphate, filtered and evaporated. Purification by chromatography (silica, 10 to 60% ethyl acetate in heptane) afforded the title compound (1.69 g, 56%) as a light yellow oil. MS: m/e=220.2 [M+H]⁺.

e) 2-Bromo-1-(1-(2-fluorophenyl)-4-methyl-1H-1,2,3-triazol-5-yl)ethanone

A solution of 1-(1-(2-fluorophenyl)-4-methyl-1H-1,2,3-triazol-5-yl)ethanone (1.66 g, 7.57 mmol) was dissolved in chloroform (12 mL) and acetic (0.24 mL) was heated to reflux and then a solution of bromine (0.41 mL, 7.95 mmol) in chloroform (5 mL) and heated under reflux for 2 h and then bromine (0.12 mL, 2.27 mmol) in chloroforom (2 mL) was added and heated under reflux for a further 30 min. After cooling to room temperature the mixture was poured onto ice-water and the mixture extracted with dichloromethane. The combined organic extracts were washed with water, brine, dried over sodium sulphate, filtered and evaporated. Purification by chromatography (silica, 10 to 60% ethyl acetate in heptane) afforded the title compound (1.54 g, 64%) as an off white solid. MS: m/e=298.1/300.0 [M+H]⁺.

f) 1-(2-Fluorophenyl)-5-(1H-imidazol-4-yl)-4-methyl-1H-1,2,3-triazole

The reaction was conducted in duplicate. A suspension of 2-bromo-1-(1-(2-fluorophenyl)-4-methyl-1H-1,2,3-triazol-5-yl)ethanone (750 mg, 2.4 mmol) in formamide (2.3 mL, 57.6 mmol) and water (0.26 mL, 14.4 mmol) was heated in the microwave to 140° C. for 3 h. After cooling to room temperature the 2 reaction mixtures were poured into HCl (1 N, 150 mL) and the mixture extracted with ethyl acetate. The aqueous phase was made alkaline with NaOH (6 N) and then extracted twice with ethyl acetate and the combined extracts washed with water, brine, dried over sodium sulphate, filtered and evaporated. Purification by chromatography (silica, ethyl acetate) afforded the title compound (597 mg, 50%) as a light yellow solid. MS: m/e=244.2 [M+H]⁺.

g) Methyl 4-(4-(1-(2-fluorophenyl)-4-methyl-1H-1,2,3-triazol-5-yl)-1H-imidazol-1-yl)benzoate A mixture of 1-(2-fluorophenyl)-5-(1H-imidazol-4-yl)-4-methyl-1H-1,2,3-triazole (290 mg, 1.19 mmol), methyl 4-fluorobenzoate (184 mg, 1.19 mmol) and potassium carbonate (330 mg, 2.38 mmol) in DMF (6.0 mL) was stirred under Ar in a sealed flask and heated at 120° C. for 2 h. After cooling to room temperature the mixture was poured into water and extracted with ethyl acetate and the combined extracts washed with water, brine, dried over sodium sulphate, filtered and evaporated. Purification by chromatography (silica, 0 to 100% ethyl acetate in heptane) afforded the title compound (8 mg, 2%) as an off white solid. MS: m/e=378.3 [M+H]⁺.

Example 34

2-{4-[3-(4-Fluoro-phenyl)-5-methyl-3H-[1,2,3]triazol-4-yl]-imidazol-1-yl}-5-trifluoromethyl-pyridine

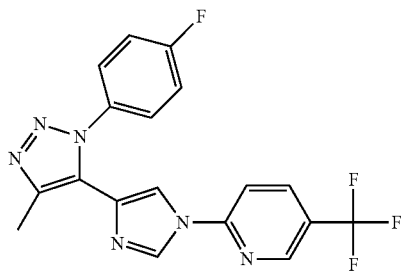 [SMILES: Cc1nnn(-c2ccc(F)cc2)c1-c1cn(-c2ccc(C(F)(F)F)cn2)cn1]

A mixture of 1-(4-fluoro-phenyl)-5-(1H-imidazol-4-yl)-4-methyl-1H-[1,2,3]triazole (100 mg, 0.411 mmol), 2-chloro-5-(trifluoromethyl)pyridine (75 mg, 0.411 mmol) and potassium carbonate (114 mg, 0.82 mmol) in DMF (2.0 mL) was stirred under Ar in a sealed flask and heated at 120° C. for 48 h. After cooling to room temperature the mixture was poured into water and the solid that formed was filtered off and purified by chromatography (silica, 0 to 100% ethyl acetate in heptane) to afford the title compound (98 mg, 60%) as a white solid. MS: m/e=389.2 [M+H]⁺.

Example 35

Methyl 6-(4-(1-(4-fluorophenyl)-4-methyl-1H-1,2,3-triazol-5-yl)-1H-imidazol-1-yl)nicotinate

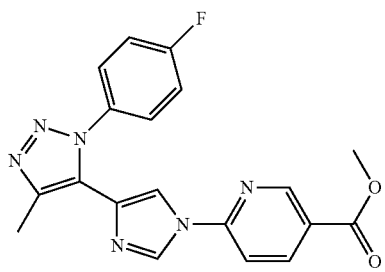 [SMILES: COC(=O)c1ccc(-n2cnc(-c3c(C)nnn3-c3ccc(F)cc3)c2)nc1]

A mixture of 1-(4-fluoro-phenyl)-5-(1H-imidazol-4-yl)-4-methyl-1H-[1,2,3]triazole (500 mg, 2.06 mmol), methyl 6-chloronicotinate (353 mg, 2.06 mmol) and potassium carbonate (568 mg, 4.11 mmol) in DMF (10 mL) was stirred under Ar in a sealed flask and heated at 120° C. for 16 h. After cooling to room temperature the mixture was poured into water (150 mL) and the solid that formed was filtered off and dried to afford the title compound (300 mg, 39%) as a light brown solid. MS: m/e=379.3 [M+H]⁺.

Example 36

6-(4-(1-(4-Fluorophenyl)-4-methyl-1H-1,2,3-triazol-5-yl)-1H-imidazol-1-yl)-N-isopropylnicotinamide

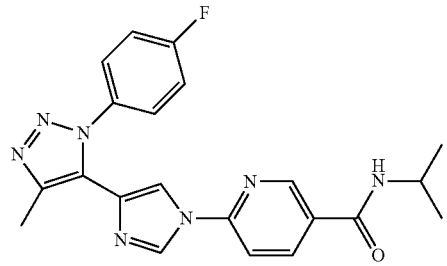 [SMILES: Cc1nnn(-c2ccc(F)cc2)c1-c1cn(-c2ccc(C(=O)NC(C)C)cn2)cn1]

a) 6-(4-(1-(4-Fluorophenyl)-4-methyl-1H-1,2,3-triazol-5-yl)-1H-imidazol-1-yl)nicotinic acid A solution of lithium hydroxide monohydrate (62 mg, 1.46 mmol) in water (2.8 mL) was added dropwise to a suspension of methyl 6-(4-(1-(4-fluorophenyl)-4-methyl-1H-1,2,3-triazol-5-yl)-1H-imidazol-1-yl)nicotinate (277 mg, 0.732 mmol) in THF (4.8 mL) and methanol (1 mL). The reaction mixture was then stirred at room temperature for 1 h and was then evaporated and the residue dissolved in water, acidified with HCl (1 N), and the resulting precipitate filtered off to afford the title product (245 mg, 92%) as a light brown solid. MS: m/e=363.2 [M−H]⁻.

b) 6-(4-(1-(4-Fluorophenyl)-4-methyl-1H-1,2,3-triazol-5-yl)-1H-imidazol-1-yl)-N-isopropylnicotinamide To a solution of 6-(4-(1-(4-fluorophenyl)-4-methyl-1H-1,2,3-triazol-5-yl)-1H-imidazol-1-yl)nicotinic acid (56 mg, 0.154 mmol) and TBTU (55 mg, 0.169 mmol) in DMF (2.0 mL) was added DIPEA (131 µL, 0.769 mmol). Then isopropylamine (15 µL, 0.169 mmol) was added and the mixture was stirred at room temperature under Ar for 1 h. The mixture was then evaporated and purification by chromatography (silica, 50 to 100% ethyl acetate in heptane) afforded the title compound (47 mg, 75%) as a white solid. MS: m/e=406.4 [M+H]+.

Example 37

6-{4-[3-(4-Fluoro-phenyl)-5-methyl-3H-[1,2,3]triazol-4-yl]-imidazol-1-yl}-N-(tetrahydropyran-4-yl)-nicotinamide

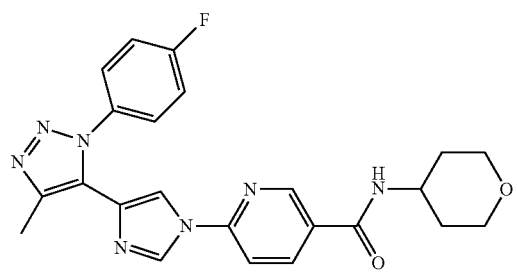 [SMILES: Cc1nnn(-c2ccc(F)cc2)c1-c1cn(-c2ccc(C(=O)NC3CCOCC3)cn2)cn1]

As described for example 36b, 6-(4-(1-(4-fluorophenyl)-4-methyl-1H-1,2,3-triazol-5-yl)-1H-imidazol-1-yl)nicotinic acid (56 mg, 0.154 mmol) was converted, using 4-aminotetrahydropyran instead of isopropylamine, to the title compound (52 mg, 76%) which was obtained as an off white solid. MS: m/e=448.3 [M+H]⁺.

Example 38

6-(4-(1-(4-Fluorophenyl)-4-methyl-1H-1,2,3-triazol-5-yl)-1H-imidazol-1-yl)-N-(3-methyloxetan-3-yl)nicotinamide

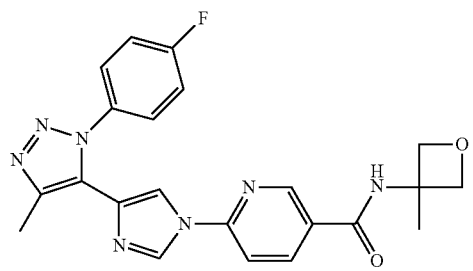 [SMILES: Cc1nnn(-c2ccc(F)cc2)c1-c1cn(-c2ccc(C(=O)NC3(C)COC3)cn2)cn1]

As described for example 36b, 6-(4-(1-(4-fluorophenyl)-4-methyl-1H-1,2,3-triazol-5-yl)-1H-imidazol-1-yl)nicotinic acid (56 mg, 0.154 mmol) was converted, using 3-methyloxetan-3-amine instead of isopropylamine, to the title compound (57 mg, 86%) which was obtained as an off white solid. MS: m/e=434.3 [M+H]+.

Example 39

(6-(4-(1-(4-Fluorophenyl)-4-methyl-1H-1,2,3-triazol-5-yl)-1H-imidazol-1-yl)pyridin-3-yl)(2-oxa-6-azaspiro[3.3]heptan-6-yl)methanone

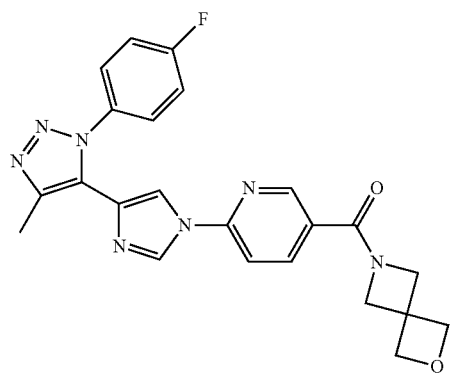 [SMILES: Cc1nnn(-c2ccc(F)cc2)c1-c1cn(-c2ccc(C(=O)N3CC4(COC4)C3)cn2)cn1]

As described for example 36b, 6-(4-(1-(4-fluorophenyl)-4-methyl-1H-1,2,3-triazol-5-yl)-1H-imidazol-1-yl)nicotinic acid (56 mg, 0.154 mmol) was converted, using 2-oxa-6-azonia-spiro[3.3]heptane oxalate salt instead of isopropylamine, to the title compound (29 mg, 42%) which was obtained as an off white solid after recrystallisation from ethyl acetate-hexane. MS: m/e=446.2 [M+H]⁺.

Example 40

6-(4-(1-(4-Fluorophenyl)-4-methyl-1H-1,2,3-triazol-5-yl)-1H-imidazol-1-yl)nicotinamide

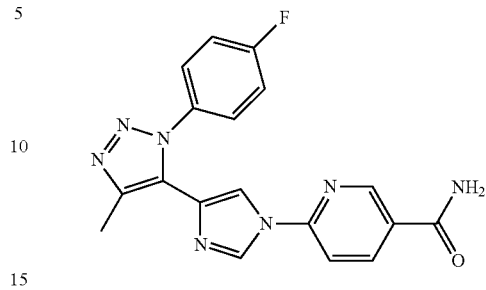

To a solution of 6-(4-(1-(4-fluorophenyl)-4-methyl-1H-1,2,3-triazol-5-yl)-1H-imidazol-1-yl)nicotinic acid (70 mg, 0.192 mmol) in DMF (2 mL) was added CDI (38 mg, 0.231 mmol) and the resulting mixture stirred at 60° C. for 1 h. After cooling to room temperature ammonium hydroxide (300 µL, 1.92 mmol) was added and reaction mixture was stirred for 16 h and then evaporated. Purification by chromatography (silica, 50 to 100% ethyl acetate in heptane) afforded the title compound (61 mg, 87%) as an off white solid. MS: m/e=364.3 [M+H]⁺.

Example 41

6-(4-(1-(4-Fluorophenyl)-4-methyl-1H-1,2,3-triazol-5-yl)-1H-imidazol-1-yl)-N-(1-hydroxy-2-methylpropan-2-yl)nicotinamide

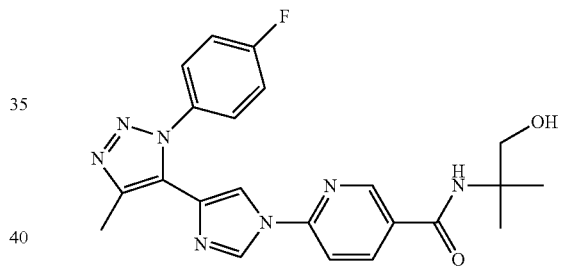

As described for example 36b, 6-(4-(1-(4-fluorophenyl)-4-methyl-1H-1,2,3-triazol-5-yl)-1H-imidazol-1-yl)nicotinic acid (65 mg, 0.178 mmol) was converted, using 2-amino-2-methyl-1-propanol instead of isopropylamine, to the title compound (61 mg, 79%) which was obtained as a white solid. MS: m/e=436.2 [M+H]⁺.

Example 42

N-Cyclopropyl-6-(4-(1-(4-fluorophenyl)-4-methyl-1H-1,2,3-triazol-5-yl)-1H-imidazol-1-yl)nicotinamide

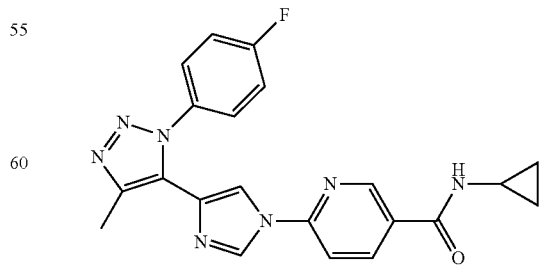

As described for example 36b, 6-(4-(1-(4-fluorophenyl)-4-methyl-1H-1,2,3-triazol-5-yl)-1H-imidazol-1-yl)nicotinic acid (65 mg, 0.178 mmol) was converted, using cyclopropylamine instead of isopropylamine, to the title compound (27 mg, 38%) which was obtained as an off white solid. MS: m/e=404.2 [M+H]⁺.

Example 43

6-(4-(1-(2-Fluorophenyl)-4-methyl-1H-1,2,3-triazol-5-yl)-1H-imidazol-1-yl)-N-isopropylnicotinamide

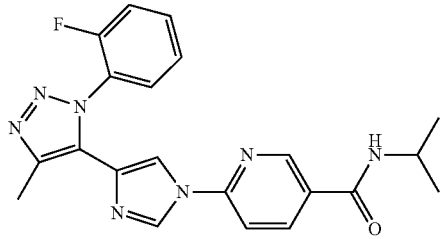 [SMILES: Cc1nnn(-c2ccccc2F)c1-c1cn(-c2ccc(C(=O)NC(C)C)cn2)cn1]

a) Methyl 6-(4-(1-(2-fluorophenyl)-4-methyl-1H-1,2,3-triazol-5-yl)-1H-imidazol-1-yl)nicotinate A mixture of 1-(2-fluorophenyl)-5-(1H-imidazol-4-yl)-4-methyl-1H-1,2,3-triazole (268 mg, 1.1 mmol), methyl 6-chloronicotinate (190 mg, 1.1 mmol) and potassium carbonate (305 mg, 2.2 mmol) in DMF (6.0 mL) was stirred under Ar in a sealed flask and heated at 120° C. for 2 h. After cooling to room temperature the mixture was poured into water and extracted with ethyl acetate and the combined extracts washed with water, brine, dried over sodium sulphate, filtered and evaporated. Purification by chromatography (silica, 10 to 100% ethyl acetate in heptane) afforded the title compound (120 mg, 29%) as an off white solid. MS: m/e=379.2 [M+H]⁺.

b) 6-(4-(1-(2-Fluorophenyl)-4-methyl-1H-1,2,3-triazol-5-yl)-1H-imidazol-1-yl)nicotinic acid A solution of lithium hydroxide monohydrate (29 mg, 0.671 mmol) in water (1.3 mL) was added dropwise to a suspension of methyl 6-(4-(1-(2-fluorophenyl)-4-methyl-1H-1,2,3-triazol-5-yl)-1H-imidazol-1-yl)nicotinate (127 mg, 0.336 mmol) in THF (5 mL) and methanol (1 mL). The reaction mixture was then stirred at room temperature for 1 h and was then evaporated and the residue dissolved in water, acidified with HCl (1 N), and the resulting precipitate filtered off to afford the title product (108 mg, 88%) as a white solid. MS: m/e=363.3 [M–H]⁻.

c) 6-(4-(1-(2-Fluorophenyl)-4-methyl-1H-1,2,3-triazol-5-yl)-1H-imidazol-1-yl)-N-isopropylnicotinamide To a solution of 6-(4-(1-(2-fluorophenyl)-4-methyl-1H-1,2,3-triazol-5-yl)-1H-imidazol-1-yl)nicotinic acid (46 mg, 0.126 mmol) and TBTU (45 mg, 0.139 mmol) in DMF (2.0 mL) was added DIPEA (110 µL, 0.631 mmol). Then isopropylamine (12 µL, 0.139 mmol) was added and the mixture was stirred at room temperature under Ar for 2 h. The mixture was then evaporated and purification by chromatography (silica, 50 to 100% ethyl acetate in heptane) afforded the title compound (34 mg, 66%) as a white foam. MS: m/e=406.3 [M+H]⁺.

Example 44

(1,1-Dioxo-1,6-thiomorpholin-4-yl)-(6-{4-[3-(4-fluoro-phenyl)-5-methyl-3H-[1,2,3]triazol-4-yl]-imidazol-1-yl}-pyridin-3-yl)-methanone

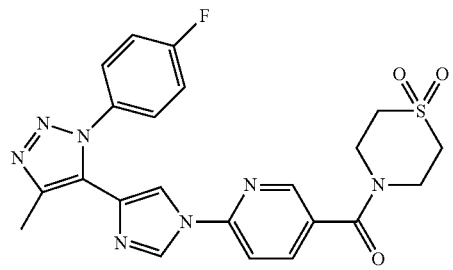 [SMILES: Cc1nnn(-c2ccc(F)cc2)c1-c1cn(-c2ccc(C(=O)N3CCS(=O)(=O)CC3)cn2)cn1]

As described for example 36b, 6-(4-(1-(4-fluorophenyl)-4-methyl-1H-1,2,3-triazol-5-yl)-1H-imidazol-1-yl)nicotinic acid (65 mg, 0.178 mmol) was converted, using thiomorpholine 1,1-dioxide instead of isopropylamine, to the title compound (32 mg, 37%) which was obtained as a white foam after purification by chromatography (HPLC reverse phase). MS: m/e=482.3 [M+H]⁺.

Example 45

6-(4-(1-(4-Fluorophenyl)-4-methyl-1H-1,2,3-triazol-5-yl)-1H-imidazol-1-yl)-N-morpholinonicotinamide

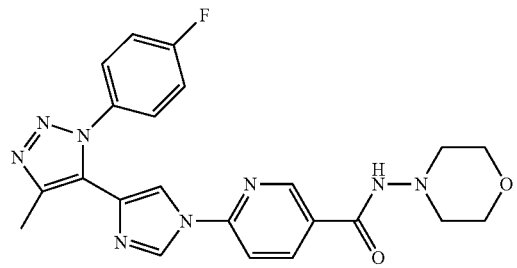 [SMILES: Cc1nnn(-c2ccc(F)cc2)c1-c1cn(-c2ccc(C(=O)NN3CCOCC3)cn2)cn1]

As described for example 36b, 6-(4-(1-(4-fluorophenyl)-4-methyl-1H-1,2,3-triazol-5-yl)-1H-imidazol-1-yl)nicotinic acid (65 mg, 0.178 mmol) was converted, using 4-aminomorpholine instead of isopropylamine, to the title compound (49 mg, 61%) which was obtained as a white solid after recrystallisation from ethyl acetate in hexane. MS: m/e=449.2 [M+H]⁺.

Example 46

6-(4-(1-(2-Fluorophenyl)-4-methyl-1H-1,2,3-triazol-5-yl)-1H-imidazol-1-yl)-N-(tetrahydro-2H-pyran-4-yl)nicotinamide

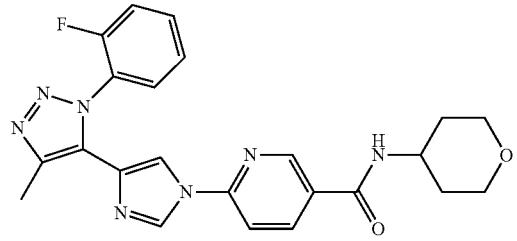 [SMILES: Cc1nnn(-c2ccccc2F)c1-c1cn(-c2ccc(C(=O)NC3CCOCC3)cn2)cn1]

As described for example 43c, 6-(4-(1-(2-fluorophenyl)-4-methyl-1H-1,2,3-triazol-5-yl)-1H-imidazol-1-yl)nicotinic acid (46 mg, 0.126 mmol) was converted, using 4-aminotetrahydropyran instead of isopropylamine, to the title compound (41 mg, 73%) which was obtained as a white foam after purification by chromatography (silica, 0-10% methanol in dichloromethane). MS: m/e=448.2 [M+H]⁺.

Example 47

6-(4-(1-(2-Fluorophenyl)-4-methyl-1H-1,2,3-triazol-5-yl)-1H-imidazol-1-yl)-N-(1-hydroxy-2-methylpropan-2-yl)nicotinamide

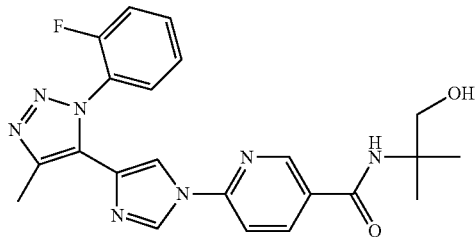 [SMILES: Cc1nnn(-c2ccccc2F)c1-c1cn(-c2ccc(C(=O)NC(C)(C)CO)cn2)cn1]

As described for example 43c, 6-(4-(1-(2-fluorophenyl)-4-methyl-1H-1,2,3-triazol-5-yl)-1H-imidazol-1-yl)nicotinic acid (74 mg, 0.203 mmol) was converted, using 2-amino-2-methylpropan-1-ol instead of isopropylamine, to the title compound (56 mg, 63%) which was obtained as a white foam after purification by chromatography (reverse phase HPLC then silica, ethyl acetate). MS: m/e=436.2 [M+H]⁺.

Example 48

6-(4-(1-(2-Fluorophenyl)-4-methyl-1H-1,2,3-triazol-5-yl)-1H-imidazol-1-yl)nicotinamide

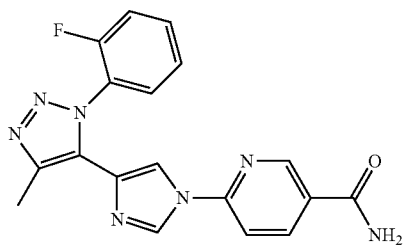 [SMILES: Cc1nnn(-c2ccccc2F)c1-c1cn(-c2ccc(C(N)=O)cn2)cn1]

To a solution of 6-(4-(1-(2-fluorophenyl)-4-methyl-1H-1,2,3-triazol-5-yl)-1H-imidazol-1-yl)nicotinic acid (74 mg, 0.203 mmol) in DMF (3 mL) was added CDI (40 mg, 0.244 mmol) and the resulting mixture stirred at 60° C. for 1 h. After cooling to room temperature ammonium hydroxide (320 µL, 2.03 mmol) was added and reaction mixture was stirred for 30 min and then evaporated. Purification by chromatography (reverse phase HPLC) afforded the title compound (58 mg, 74%) as a white solid. MS: m/e=364.1 [M+H]⁺.

Example 49

(6-(4-(1-(2-Fluorophenyl)-4-methyl-1H-1,2,3-triazol-5-yl)-1H-imidazol-1-yl)pyridin-3-yl)(2-oxa-6-azaspiro[3.3]heptan-6-yl)methanone

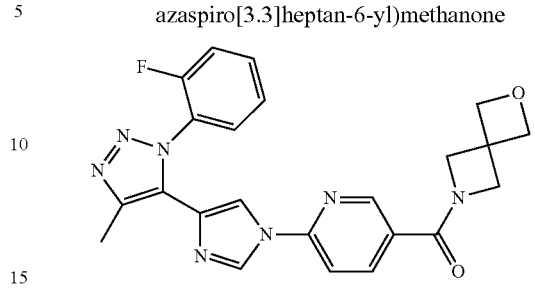

As described for example 43c, 6-(4-(1-(2-fluorophenyl)-4-methyl-1H-1,2,3-triazol-5-yl)-1H-imidazol-1-yl)nicotinic acid (74 mg, 0.203 mmol) was converted, using 2-oxa-6-azonia-spiro[3.3]heptane oxalate salt instead of isopropylamine, to the title compound (50 mg, 55%) which was obtained as a white solid after purification by chromatography (reverse phase HPLC). MS: m/e=446.2 [M+H]⁺.

Example 50

6-(4-(1-(2-Fluorophenyl)-4-methyl-1H-1,2,3-triazol-5-yl)-1H-imidazol-1-yl)-N-(3-methyloxetan-3-yl)nicotinamide

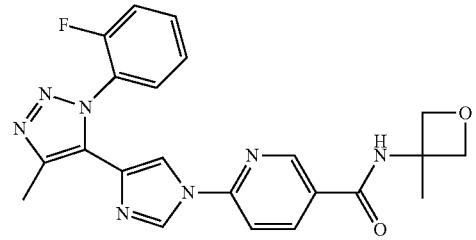 [SMILES: Cc1nnn(-c2ccccc2F)c1-c1cn(-c2ccc(C(=O)NC3(C)COC3)cn2)cn1]

As described for example 43c, 6-(4-(1-(2-fluorophenyl)-4-methyl-1H-1,2,3-triazol-5-yl)-1H-imidazol-1-yl)nicotinic acid (74 mg, 0.203 mmol) was converted, using methyl-3-oxetanamine instead of isopropylamine, to the title compound (70 mg, 80%) which was obtained as a white foam after purification by chromatography (reverse phase HPLC). MS: m/e=434.3 [M+H]⁺.

Example 51

6-(4-(1-(2-Fluorophenyl)-4-methyl-1H-1,2,3-triazol-5-yl)-1H-imidazol-1-yl)-N-morpholinonicotinamide

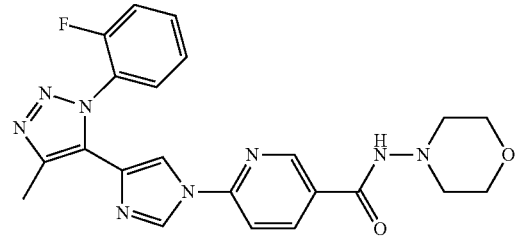 [SMILES: Cc1nnn(-c2ccccc2F)c1-c1cn(-c2ccc(C(=O)NN3CCOCC3)cn2)cn1]

As described for example 43c, 6-(4-(1-(2-fluorophenyl)-4-methyl-1H-1,2,3-triazol-5-yl)-1H-imidazol-1-yl)nicotinic acid (74 mg, 0.203 mmol) was converted, using 4-aminomorpholine instead of isopropylamine, to the title compound (56 mg, 62%) which was obtained as a white foam after purification by chromatography (reverse phase HPLC then silica, ethyl acetate). MS: m/e=449.2 [M+H]⁺.

Example 52

N-Cyclopropyl-6-(4-(1-(2-fluorophenyl)-4-methyl-1H-1,2,3-triazol-5-yl)-1H-imidazol-1-yl)nicotinamide

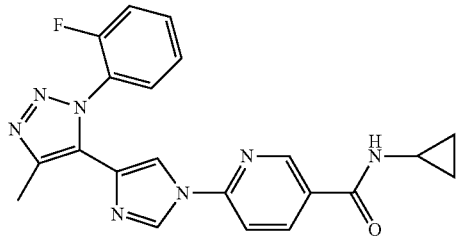 [SMILES: Cc1nnn(-c2ccccc2F)c1-c1cn(-c2ccc(C(=O)NC3CC3)cn2)cn1]

As described for example 43c, 6-(4-(1-(2-fluorophenyl)-4-methyl-1H-1,2,3-triazol-5-yl)-1H-imidazol-1-yl)nicotinic acid (74 mg, 0.203 mmol) was converted, using cyclopropylamine instead of isopropylamine, to the title compound (42 mg, 51%) which was obtained as a white foam after purification by chromatography (reverse phase HPLC then silica, ethyl acetate). MS: m/e=404.4 [M+H]⁺.

Example 53

N-(Cyclopropylmethyl)-6-(4-(1-(2-fluorophenyl)-4-methyl-1H-1,2,3-triazol-5-yl)-1H-imidazol-1-yl)nicotinamide

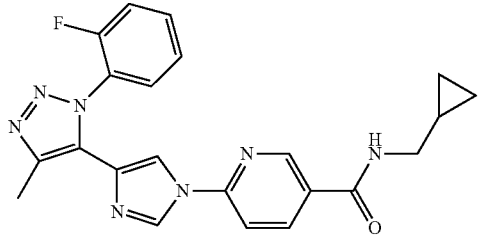 [SMILES: Cc1nnn(-c2ccccc2F)c1-c1cn(-c2ccc(C(=O)NCC3CC3)cn2)cn1]

As described for example 43c, 6-(4-(1-(2-fluorophenyl)-4-methyl-1H-1,2,3-triazol-5-yl)-1H-imidazol-1-yl)nicotinic acid (74 mg, 0.203 mmol) was converted, using aminomethylcyclopropane instead of isopropylamine, to the title compound (40 mg, 47%) which was obtained as a white foam after purification by chromatography (reverse phase HPLC). MS: m/e=418.3 [M+H]⁺.

Biochemical Assay

The ability of compounds present invention to bind to GABA A receptor subtypes was determined by competition for [³H]flumazenil (85 Ci/mmol; Roche) binding to HEK293 cells expressing rat (stably transfected) or human (transiently transfected) receptors of composition α1β2/3γ2, α2β3γ2, α3β3γ2 and α5β3γ2.

Membrane Preparation

Cell pellets were suspended in Krebs-tris buffer (4.8 mM KCl, 1.2 mM CaCl₂, 1.2 mM MgCl₂, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand Binding Assay

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of 10-10⁻³×10⁻⁶ M. Nonspecific binding was defined by 10⁻⁵ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting.

Data Calculation $K_i$ values were calculated using Excel-Fit (Microsoft) and are the means of two determinations.

The compounds of the accompanying examples were tested in the above described assay, and the particular compounds were found to possess a $K_i$ value for displacement of [³H]flumazenil from α5 subunits of the rat GABA A receptor of 100 nM or less. A particular embodiment embraces compounds with a $K_i$ of 35 nM or less. In a particular embodiment the compounds of the invention are binding selectively for the α5 subunit relative to the α1, α2 and α3 subunit.

Representative test results, obtained by the above described assay measuring binding affinity to HEK293 cells expressing human (h) receptors, are shown in Table 1 below.

TABLE 1

Binding affinities to HEK293 cells expressing human (h) receptors of representative examples.

| Ex. | hKi (GABA Aα5) |
| --- | --- |
| 1 | 27.2 |
| 2 | 41.2 |
| 3 | 21.1 |
| 4 | 36.6 |
| 5 | 23.8 |
| 6 | 51.3 |
| 7 | 18.8 |
| 8 | 84.3 |
| 9 | 76.3 |
| 10 | 29.6 |
| 11 | 14.7 |
| 12 | 33 |
| 13 | 14.6 |
| 14 | 37.6 |
| 15 | 82.2 |
| 16 | 12.1 |
| 17 | 68.8 |
| 18 | 75.1 |
| 19 | 66.2 |
| 20 | 16.2 |
| 21 | 86 |
| 22 | 43.3 |
| 23 | 54.9 |
| 24 | 21.3 |
| 25 | 19.3 |
| 26 | 66.5 |
| 27 | 16.1 |
| 28 | 32.4 |
| 29 | 9.5 |
| 30 | 65 |
| 31 | 49.2 |
| 32 | 25.9 |
| 33 | 34.5 |
| 34 | 45.6 |
| 35 | 26.3 |

TABLE 1-continued

Binding affinities to HEK293 cells expressing
human (h) receptors of representative examples.

| Ex. | hKi (GABA Aa5) |
|---|---|
| 36 | 6.2 |
| 37 | 25.9 |
| 38 | 9.6 |
| 39 | 35.8 |
| 40 | 12.6 |
| 41 | 20.8 |
| 42 | 3.2 |
| 43 | 15.1 |
| 44 | 29 |
| 45 | 69.4 |
| 46 | 49 |
| 47 | 51.7 |
| 48 | 17.8 |
| 49 | 90 |
| 50 | 17.9 |
| 51 | 50.5 |
| 52 | 10.9 |
| 53 | 32.7 |

The invention claimed is:

1. A compound of formula (I)

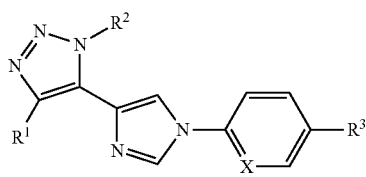

wherein
X is N or CH;
$R^1$ and $R^2$ are each independently alkyl, aryl optionally substituted by 1 or 2 halo, or heteroaryl optionally substituted by 1 or 2 halo, wherein one of $R^1$ and $R^2$ is alkyl;
$R^3$ is halo, alkyl, haloalkyl, hydroxyalkyl, cyano, nitro, —C(O)$R^4$, or —C(O)N$R^5R^6$;
$R^4$ is hydrogen, alkyl, aryl, hydroxy, alkoxy or aryloxy;
$R^5$ is hydrogen, alkyl, haloalkyl, hydroxyalkyl, —(CH$_2$)$_n$-cycloalkyl, —(CH$_2$)$_n$-heterocycloalkyl, —(CH$_2$)$_n$-aryl, —(CH$_2$)$_n$-heteroaryl, —(CH$_2$)$_m$—N$R^7R^8$, —(CH$_2$)$_m$—O$R^9$, wherein cycloalkyl, heterocycloalkyl, aryl and heteroaryl are each optionally substituted by one or more halo, alkyl, haloalkyl, hydroxyalkyl, alkoxy, hydroxy, or oxo;
n is an integer from 0 to 6;
m is an integer from 2 to 6;
$R^6$, $R^7$, $R^8$, and $R^9$ are each independently hydrogen, alkyl, or aryl;
or $R^5$ and $R^6$ together with the nitrogen to which they are bound form a heterocycloalkyl, or heteroaryl, wherein heterocycloalkyl and heteroaryl are optionally substituted by one or more halo, alkyl, haloalkyl, hydroxyalkyl, alkoxy, hydroxy, or oxo;
or a pharmaceutically acceptable salt or ester thereof.

2. The compound of claim 1, wherein
X is N or CH;
$R^1$ and $R^2$ are each independently alkyl, or aryl optionally substituted by 1 halo, wherein one of $R^1$ and $R^2$ is alkyl;
$R^3$ is haloalkyl, nitro, —C(O)$R^4$, or —C(O)N$R^5R^6$;
$R^4$ is alkyl, hydroxy, or alkoxy;

$R^5$ is hydrogen, alkyl, hydroxyalkyl, —(CH$_2$)$_n$-cycloalkyl, or —(CH$_2$)$_n$-heterocycloalkyl, wherein heterocycloalkyl is optionally substituted by one alkyl;
n is an integer from 0 to 1;
$R^6$ is hydrogen;
or $R^5$ and $R^6$ together with the nitrogen to which they are bound form a heterocycloalkyl optionally substituted by one or more oxo;
or a pharmaceutically acceptable salt or ester thereof.

3. The compound of claim 1, wherein X is N.

4. The compound of claim 1, wherein one of $R^1$ and $R^2$ is alkyl, and the other one is aryl optionally substituted by one halo.

5. The compound of claim 4, wherein $R^1$ is methyl, and $R^2$ is phenyl substituted by one fluoro.

6. The compound of claim 4, wherein $R^2$ is methyl, and $R^1$ is phenyl substituted by one fluoro.

7. The compound of claim 1, wherein $R^3$ is haloalkyl, nitro, —C(O)$R^4$, or —C(O)N$R^5R^6$.

8. The compound of claim 7, wherein $R^3$ is —C(O)N$R^5R^6$.

9. The compound of claim 1, wherein $R^4$ is alkyl, hydroxy, or alkoxy.

10. The compound of claim 9, wherein $R^4$ is methyl, hydroxy, or methoxy.

11. The compound of claim 1, wherein $R^5$ is hydrogen, alkyl, hydroxyalkyl, —(CH$_2$)$_n$-cycloalkyl, or —(CH$_2$)$_n$-heterocycloalkyl, wherein heterocycloalkyl is optionally substituted by one alkyl.

12. The compound of claim 11, wherein $R^5$ is hydrogen, isopropyl, iso-butyl substituted by hydroxy, tert-butyl substituted by hydroxy, cyclopropyl, cyclopropylmethyl, morpholinyl, tetrahydropyranyl, or oxetanyl substituted by methyl.

13. The compound of claim 1, wherein $R^6$ is hydrogen.

14. The compound of claim 1, wherein $R^5$ and $R^6$ together with the nitrogen to which they are bound form a heterocycloalkyl optionally substituted by one or more oxo.

15. The compound of claim 14, wherein $R^5$ and $R^6$ together with the nitrogen to which they are bound form 1,1-dioxo-1,6-thiomorpholin-4-yl or 2-oxa-6-aza-spiro[3.3]hept-6-yl.

16. The compound of claim 1, selected from the group consisting of:
1-(4-{4-[5-(4-Fluoro-phenyl)-3-methyl-3H-[1,2,3]triazol-4-yl]-imidazol-1-yl}-phenyl)-ethanone;
4-{4-[5-(4-Fluoro-phenyl)-3-methyl-3H-[1,2,3]triazol-4-yl]-imidazol-1-yl}-benzoic acid methyl ester;
4-{4-[5-(4-Fluoro-phenyl)-3-methyl-3H-[1,2,3]triazol-4-yl]-imidazol-1-yl}-N-isopropyl-benzamide;
4-{4-[5-(4-Fluoro-phenyl)-3-methyl-3H-[1,2,3]triazol-4-yl]-imidazol-1-yl}-N-(tetrahydro-pyran-4-yl)-benzamide;
4-{4-[5-(4-Fluoro-phenyl)-3-methyl-3H-[1,2,3]triazol-4-yl]-imidazol-1-yl}-N-(3-methyl-oxetan-3-yl)-benzamide;
(4-{4-[5-(4-Fluoro-phenyl)-3-methyl-3H-[1,2,3]triazol-4-yl]-imidazol-1-yl}-phenyl)-(2-oxa-6-aza-spiro[3.3]hept-6-yl)-methanone;
4-{4-[5-(4-Fluoro-phenyl)-3-methyl-3H-[1,2,3]triazol-4-yl]-imidazol-1-yl}-benzamide;
4-(2-Fluorophenyl)-1-methyl-5-(1-(4-(trifluoromethyl)phenyl)-1H-imidazol-4-yl)-1H-1,2,3-triazole;
4-(2-Fluorophenyl)-1-methyl-5-(1-(4-nitrophenyl)-1H-imidazol-4-yl)-1H-1,2,3-triazole;
1-(4-(4-(4-(2-Fluorophenyl)-1-methyl-1H-1,2,3-triazol-5-yl)-1H-imidazol-1-yl)phenyl)ethanone;
and 6-{4-[5-(4-Fluoro-phenyl)-3-methyl-3H-[1,2,3]triazol-4-yl]-imidazol-1-yl}-N-isopropyl-nicotinamide or a pharmaceutically acceptable salt or ester thereof.

17. The compound of claim 1, selected from the group consisting of:

6-{4-[5-(4-Fluoro-phenyl)-3-methyl-3H-[1,2,3]triazol-4-yl]-imidazol-1-yl}-N-(tetrahydro-pyran-4-yl)-nicotinamide;
6-{4-[5-(4-Fluoro-phenyl)-3-methyl-3H-[1,2,3]triazol-4-yl]-imidazol-1-yl}-N-(3-methyl-oxetan-3-yl)-nicotinamide;
(6-{4-[5-(4-Fluoro-phenyl)-3-methyl-3H-[1,2,3]triazol-4-yl]-imidazol-1-yl}-pyridin-3-yl)-(2-oxa-6-aza-spiro[3.3]hept-6-yl)-methanone;
2-{4-[5-(4-Fluoro-phenyl)-3-methyl-3H-[1,2,3]triazol-4-yl]-imidazol-1-yl}-5-trifluoromethyl-pyridine;
6-(4-(4-(4-Fluorophenyl)-1-methyl-1H-1,2,3-triazol-5-yl)-1H-imidazol-1-yl)nicotinamide;
Methyl 6-(4-(4-(2-chlorophenyl)-1-methyl-1H-1,2,3-triazol-5-yl)-1H-imidazol-1-yl)nicotinate;
6-(4-(4-(2-Chlorophenyl)-1-methyl-1H-1,2,3-triazol-5-yl)-1H-imidazol-1-yl)-N-isopropylnicotinamide;
6-(4-(4-(2-Chlorophenyl)-1-methyl-1H-1,2,3-triazol-5-yl)-1H-imidazol-1-yl)nicotinamide;
Methyl 6-(4-(4-(2-fluorophenyl)-1-methyl-1H-1,2,3-triazol-5-yl)-1H-imidazol-1-yl)nicotinate;
6-(4-(4-(2-Fluorophenyl)-1-methyl-1H-1,2,3-triazol-5-yl)-1H-imidazol-1-yl)nicotinic acid; and
6-(4-(4-(2-Fluorophenyl)-1-methyl-1H-1,2,3-triazol-5-yl)-1H-imidazol-1-yl)-N-(tetrahydro-2H-pyran-4-yl)nicotinamide or a pharmaceutically acceptable salt or ester thereof.

18. The compound of claim 1, selected from the group consisting of:

6-(4-(4-(2-Fluorophenyl)-1-methyl-1H-1,2,3-triazol-5-yl)-1H-imidazol-1-yl)-N-isopropylnicotinamide;
6-(4-(4-(2-Fluorophenyl)-1-methyl-1H-1,2,3-triazol-5-yl)-1H-imidazol-1-yl)-N-(2-hydroxy-2-methylpropyl)nicotinamide;
6-(4-(4-(2-Fluorophenyl)-1-methyl-1H-1,2,3-triazol-5-yl)-1H-imidazol-1-yl)nicotinamide;
(6-(4-(4-(2-Fluorophenyl)-1-methyl-1-1,2,3-triazol-5-yl)-1H-imidazol-1-yl)pyridin-3-yl)(2-oxa-6-azaspiro[3.3]heptan-6-yl)methanone;
6-(4-(4-(2-Fluorophenyl)-1-methyl-1H-1,2,3-triazol-5-yl)-1H-imidazol-1-yl)-N-(3-methyloxetan-3-yl)nicotinamide;
6-(4-(4-(2-Fluorophenyl)-1-methyl-1H-1,2,3-triazol-5-yl)-1H-imidazol-1-yl)-N-morpholinonicotinamide;
N-Cyclopropyl-6-(4-(4-(2-fluorophenyl)-1-methyl-1H-1,2,3-triazol-5-yl)-1H-imidazol-1-yl)nicotinamide;
2-(4-(4-(2-Fluorophenyl)-1-methyl-1H-1,2,3-triazol-5-yl)-1H-imidazol-1-yl)-5-(trifluoromethyl)pyridine;
1-(4-Fluoro-phenyl)-4-methyl-5-[1-(4-trifluoromethyl-phenyl)-1H-imidazol-4-yl]-1H-[1,2,3]triazole; and
1-(4-{4-[3-(4-Fluoro-phenyl)-5-methyl-3H-[1,2,3]triazol-4-yl]-imidazol-1-yl}-phenyl)-ethanone or a pharmaceutically acceptable salt or ester thereof.

19. The compound of claim 1, selected from the group consisting of

Methyl 4-(4-(1-(2-fluorophenyl)-4-methyl-1H-1,2,3-triazol-5-yl)-1H-imidazol-1-yl)benzoate;
2-{4-[3-(4-Fluoro-phenyl)-5-methyl-3H-[1,2,3]triazol-4-yl]-imidazol-1-yl}-5-trifluoromethyl-pyridine;
Methyl 6-(4-(1-(4-fluorophenyl)-4-methyl-1H-1,2,3-triazol-5-yl)-1H-imidazol-1-yl)nicotinate;
6-(4-(1-(4-Fluorophenyl)-4-methyl-1H-1,2,3-triazol-5-yl)-1H-imidazol-1-yl)-N-isopropylnicotinamide;
6-{4-[3-(4-Fluoro-phenyl)-5-methyl-3H-[1,2,3]triazol-4-yl]-imidazol-1-yl}-N-(tetrahydro-pyran-4-yl)-nicotinamide;
6-(4-(1-(4-Fluorophenyl)-4-methyl-1H-1,2,3-triazol-5-yl)-1H-imidazol-1-yl)-N-(3-methyloxetan-3-yl)nicotinamide;
(6-(4-(1-(4-Fluorophenyl)-4-methyl-1H-1,2,3-triazol-5-yl)-1H-imidazol-1-yl)pyridin-3-yl)(2-oxa-6-azaspiro[3.3]heptan-6-yl)methanone;
6-(4-(1-(4-Fluorophenyl)-4-methyl-1H-1,2,3-triazol-5-yl)-1H-imidazol-1-yl)nicotinamide;
6-(4-(1-(4-Fluorophenyl)-4-methyl-1H-1,2,3-triazol-5-yl)-1H-imidazol-1-yl)-N-(1-hydroxy-2-methylpropan-2-yl)nicotinamide; and
N-Cyclopropyl-6-(4-(1-(4-fluorophenyl)-4-methyl-1H-1,2,3-triazol-5-yl)-1H-imidazol-1-yl)nicotinamide or a pharmaceutically acceptable salt or ester thereof.

20. The compound of claim 1, selected from the group consisting of:

6-(4-(1-(2-Fluorophenyl)-4-methyl-1H-1,2,3-triazol-5-yl)-1H-imidazol-1-yl)-N-isopropylnicotinamide;
(1,1-Dioxo-1,6-thiomorpholin-4-yl)-(6-{4-[3-(4-fluoro-phenyl)-5-methyl-3H-[1,2,3]triazol-4-yl]-imidazol-1-yl}-pyridin-3-yl)-methanone;
6-(4-(1-(4-Fluorophenyl)-4-methyl-1H-1,2,3-triazol-5-yl)-1H-imidazol-1-yl)-N-morpholinonicotinamide;
6-(4-(1-(2-Fluorophenyl)-4-methyl-1H-1,2,3-triazol-5-yl)-1H-imidazol-1-yl)-N-(tetrahydro-2H-pyran-4-yl)nicotinamide;
6-(4-(1-(2-Fluorophenyl)-4-methyl-1H-1,2,3-triazol-5-yl)-1H-imidazol-1-yl)-N-(1-hydroxy-2-methylpropan-2-yl)nicotinamide;
6-(4-(1-(2-Fluorophenyl)-4-methyl-1H-1,2,3-triazol-5-yl)-1H-imidazol-1-yl)nicotinamide;
(6-(4-(1-(2-Fluorophenyl)-4-methyl-1H-1,2,3-triazol-5-yl)-1H-imidazol-1-yl)pyridin-3-yl)(2-oxa-6-azaspiro[3.3]heptan-6-yl)methanone;
6-(4-(1-(2-Fluorophenyl)-4-methyl-1H-1,2,3-triazol-5-yl)-1H-imidazol-1-yl)-N-(3-methyloxetan-3-yl)nicotinamide;
6-(4-(1-(2-Fluorophenyl)-4-methyl-1H-1,2,3-triazol-5-yl)-1H-imidazol-1-yl)-N-morpholinonicotinamide;
N-Cyclopropyl-6-(4-(1-(2-fluorophenyl)-4-methyl-1H-1,2,3-triazol-5-yl)-1H-imidazol-1-yl)nicotinamide; and
N-(Cyclopropylmethyl)-6-(4-(1-(2-fluorophenyl)-4-methyl-1H-1,2,3-triazol-5-yl)-1H-imidazol-1-yl)nicotinamide;

or a pharmaceutically acceptable salt or ester thereof.

21. The compound of claim 1, selected from the group consisting of:

4-{4-[5-(4-Fluoro-phenyl)-3-methyl-3H-[1,2,3]triazol-4-yl]-imidazol-1-yl}-N-isopropyl-benzamide;
6-{4-[5-(4-Fluoro-phenyl)-3-methyl-3H-[1,2,3]triazol-4-yl]-imidazol-1-yl}-N-isopropyl-nicotinamide;
6-{4-[5-(4-Fluoro-phenyl)-3-methyl-3H-[1,2,3]triazol-4-yl]-imidazol-1-yl}-N-(3-methyl-oxetan-3-yl)-nicotinamide;
(6-{4-[5-(4-Fluoro-phenyl)-3-methyl-3H-[1,2,3]triazol-4-yl]-imidazol-1-yl}-pyridin-3-yl)-(2-oxa-6-aza-spiro[3.3]hept-6-yl)-methanone;
2-{4-[3-(4-Fluoro-phenyl)-5-methyl-3H-[1,2,3]triazol-4-yl]-imidazol-1-yl}-5-trifluoromethyl-pyridine;
6-(4-(1-(4-Fluorophenyl)-4-methyl-1H-1,2,3-triazol-5-yl)-1H-imidazol-1-yl)-N-isopropylnicotinamide;

6-{4-[3-(4-Fluoro-phenyl)-5-methyl-3H-[1,2,3]triazol-4-yl]-imidazol-1-yl}-N-(tetrahydro-pyran-4-yl)-nicotinamide;

6-(4-(1-(4-Fluorophenyl)-4-methyl-1H-1,2,3-triazol-5-yl)-1H-imidazol-1-yl)-N-(3-methyloxetan-3-yl)nicotinamide;

(6-(4-(1-(4-Fluorophenyl)-4-methyl-1H-1,2,3-triazol-5-yl)-1H-imidazol-1-yl)pyridin-3-yl)(2-oxa-6-azaspiro[3.3]heptan-6-yl)methanone;

6-(4-(1-(4-Fluorophenyl)-4-methyl-1H-1,2,3-triazol-5-yl)-1H-imidazol-1-yl)-N-(1-hydroxy-2-methylpropan-2-yl)nicotinamide; and N-Cyclopropyl-6-(4-(1-(4-fluorophenyl)-4-methyl-1H-1,2,3-triazol-5-yl)-1H-imidazol-1-yl)nicotinamide;

or a pharmaceutically acceptable salt or ester thereof.

22. A pharmaceutical composition comprising a therapeutically effective amount of a compound of formula (I)

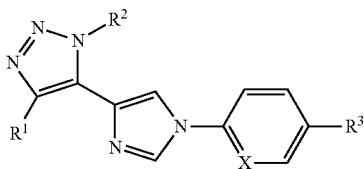

(I)

wherein

X is N or CH;

$R^1$ and $R^2$ are each independently alkyl, aryl optionally substituted by 1 or 2 halo, or heteroaryl optionally substituted by 1 or 2 halo, wherein one of $R^1$ and $R^2$ is alkyl;

$R^3$ is halo, alkyl, haloalkyl, hydroxyalkyl, cyano, nitro, —C(O)$R^4$, or —C(O)N$R^5R^6$;

$R^4$ is hydrogen, alkyl, aryl, hydroxy, alkoxy or aryloxy;

$R^5$ is hydrogen, alkyl, haloalkyl, hydroxyalkyl, —(CH$_2$)$_n$-cycloalkyl, —(CH$_2$)$_n$-heterocycloalkyl, —(CH$_2$)$_n$-aryl, —(CH$_2$)$_n$-heteroaryl, —(CH$_2$)$_m$—NR$^7$R$^8$, —(CH$_2$)$_m$—OR$^9$, wherein cycloalkyl, heterocycloalkyl, aryl and heteroaryl are each optionally substituted by one or more halo, alkyl, haloalkyl, hydroxyalkyl, alkoxy, hydroxy, or oxo;

n is an integer from 0 to 6;

m is an integer from 2 to 6;

$R^6$, $R^7$, $R^8$, and $R^9$ are each independently hydrogen, alkyl, or aryl;

or $R^5$ and $R^6$ together with the nitrogen to which they are bound form a heterocycloalkyl, or heteroaryl, wherein heterocycloalkyl and heteroaryl are optionally substituted by one or more halo, alkyl, haloalkyl, hydroxyalkyl, alkoxy, hydroxy, or oxo;

or a pharmaceutically acceptable salt or ester thereof and a pharmaceutically acceptable carrier.

* * * * *